US008500823B2

(12) United States Patent
Herr et al.

(10) Patent No.: US 8,500,823 B2
(45) Date of Patent: Aug. 6, 2013

(54) POWERED ARTIFICIAL KNEE WITH AGONIST-ANTAGONIST ACTUATION

(75) Inventors: Hugh M. Herr, Somerville, MA (US); Ernesto C. Martinez-Villalpando, Cambridge, MA (US); Jeff Anthony Weber, San Francisco, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/697,894

(22) Filed: Feb. 1, 2010

(65) Prior Publication Data
US 2010/0312363 A1  Dec. 9, 2010

Related U.S. Application Data

(63) Continuation-in-part of application No. 12/608,627, filed on Oct. 29, 2009, which is a continuation of
(Continued)

(51) Int. Cl.
*A61F 2/62* (2006.01)
(52) U.S. Cl.
USPC .......... 623/39; 623/43; 623/44; 623/46; 623/24
(58) Field of Classification Search
USPC ........................... 623/24–27, 39–43, 46
See application file for complete search history.

(56) References Cited

U.S. PATENT DOCUMENTS

| 2,489,291 A | 11/1949 | Henschke et al. |
| 2,529,968 A | 11/1950 | Sartin |

(Continued)

FOREIGN PATENT DOCUMENTS

| EP | 1393866 | 3/2004 |
| EP | 1408892 | 4/2004 |

(Continued)

OTHER PUBLICATIONS

Office action mailed Jan. 23, 2012, U.S. Appl. No. 12/608,627, filed Oct. 29, 2009.

(Continued)

*Primary Examiner* — David Isabella
*Assistant Examiner* — Marcia Hoffman
(74) *Attorney, Agent, or Firm* — Hamilton, Brook, Smith & Reynolds, P.C.

(57) ABSTRACT

A knee prosthesis comprises an agonist-antagonist arrangement of two series-elastic actuators in parallel, including a knee joint, flexion and extension actuators connected to the joint in parallel with a leg member, and a controller for independently energizing the actuators to control the movement of the knee joint and leg. The flexion actuator comprises the series combination of a flexion motor and a flexion elastic element and the extension actuator comprises the series combination of an extension motor and an extension elastic element. Sensors provide feedback to the controller. The flexion actuator and the extension actuator may be unidirectional, with the flexion and extension elastic elements being series springs. The extension actuator may alternatively be bidirectional, with the extension elastic element being a set of precompressed series springs. Alternatively, the flexion elastic element may be a non-linear softening spring and the extension elastic element may be a non-linear hardening spring.

1 Claim, 15 Drawing Sheets

Related U.S. Application Data application No. 11/642,993, filed on Dec. 19, 2006, now abandoned, which is a continuation-in-part of application No. 11/395,448, filed on Mar. 31, 2006, now abandoned, and a continuation-in-part of application No. 11/495,140, filed on Jul. 29, 2006, now abandoned, and a continuation-in-part of application No. 11/600,291, filed on Nov. 15, 2006, now abandoned, and a continuation-in-part of application No. 11/499,853, filed on Aug. 4, 2006, now Pat. No. 7,313,463, which is a continuation-in-part of application No. 11/395,448, filed on Mar. 31, 2006, now abandoned, application No. 12/697,894, which is a continuation-in-part of application No. 11/395,448, filed on Mar. 31, 2006, now abandoned, application No. 12/697,894, which is a continuation-in-part of application No. 11/495,140, filed on Jul. 29, 2006, now abandoned, which is a continuation-in-part of application No. 11/395,448, filed on Mar. 31, 2006, now abandoned, application No. 12/697,894, which is a continuation-in-part of application No. 11/600,291, filed on Nov. 15, 2006, now abandoned, which is a continuation-in-part of application No. 11/395,448, filed on Mar. 31, 2006, now abandoned, and a continuation-in-part of application No. 11/499,853, filed on Aug. 4, 2006, now Pat. No. 7,313,463, and a continuation-in-part of application No. 11/495,140, filed on Jul. 29, 2006, now abandoned.

(60) Provisional application No. 61/148,545, filed on Jan. 30, 2009, provisional application No. 60/751,680, filed on Dec. 19, 2005, provisional application No. 60/705,651, filed on Aug. 4, 2005, provisional application No. 60/666,876, filed on Mar. 31, 2005, provisional application No. 60/704,517, filed on Aug. 1, 2005, provisional application No. 60/736,929, filed on Nov. 15, 2005.

(56) References Cited

U.S. PATENT DOCUMENTS

| | | |
|---|---|---|
| 3,098,645 A | 7/1963 | Owens |
| 3,207,497 A | 9/1965 | Schoonover |
| 3,844,279 A | 10/1974 | Konvalin |
| 4,442,390 A | 4/1984 | Davis |
| 4,463,291 A | 7/1984 | Usry |
| 4,518,307 A | 5/1985 | Bloch |
| 4,532,462 A | 7/1985 | Washbourn et al. |
| 4,546,295 A | 10/1985 | Wickham et al. |
| 4,546,296 A | 10/1985 | Washbourn et al. |
| 4,546,297 A | 10/1985 | Washbourn et al. |
| 4,546,298 A | 10/1985 | Wickham et al. |
| 4,569,352 A | 2/1986 | Petrofsky et al. |
| 4,600,357 A | 7/1986 | Coules |
| 4,657,470 A | 4/1987 | Clarke et al. |
| 4,843,921 A | 7/1989 | Kremer |
| 4,865,376 A | 9/1989 | Leaver et al. |
| 4,872,803 A | 10/1989 | Asakawa |
| 4,909,535 A | 3/1990 | Clark et al. |
| 4,921,293 A | 5/1990 | Ruoff et al. |
| 4,921,393 A | 5/1990 | Andeen et al. |
| 4,923,474 A | 5/1990 | Klasson et al. |
| 4,923,475 A | 5/1990 | Gosthnian et al. |
| 4,936,295 A | 6/1990 | Crane |
| 4,964,402 A | 10/1990 | Grim et al. |
| 4,989,161 A | 1/1991 | Oaki |
| 5,012,591 A | 5/1991 | Asakawa |
| 5,049,797 A | 9/1991 | Phillips |
| 5,062,673 A | 11/1991 | Mimura |
| 5,088,478 A | 2/1992 | Grim |
| 5,092,902 A | 3/1992 | Adams et al. |
| 5,112,296 A | 5/1992 | Beard et al. |
| 5,174,168 A | 12/1992 | Takagi et al. |
| 5,181,933 A | 1/1993 | Phillips |
| 5,252,102 A | 10/1993 | Singer et al. |
| 5,294,873 A | 3/1994 | Seraji |
| RE34,661 E | 7/1994 | Grim |
| 5,327,790 A | 7/1994 | Levin et al. |
| 5,367,790 A | 11/1994 | Gamow et al. |
| 5,383,939 A | 1/1995 | James |
| 5,405,409 A | 4/1995 | Knoth |
| 5,442,270 A | 8/1995 | Tetsuaki |
| 5,443,521 A | 8/1995 | Knoth et al. |
| 5,456,341 A | 10/1995 | Garnjost et al. |
| 5,458,143 A | 10/1995 | Herr |
| 5,476,441 A | 12/1995 | Durfee et al. |
| 5,502,363 A | 3/1996 | Tasch et al. |
| 5,514,185 A | 5/1996 | Phillips |
| 5,556,422 A | 9/1996 | Powell, III et al. |
| 5,571,205 A | 11/1996 | James |
| 5,643,332 A | 7/1997 | Stein |
| 5,650,704 A | 7/1997 | Pratt et al. |
| 5,662,693 A | 9/1997 | Johnson et al. |
| 5,701,686 A | 12/1997 | Herr et al. |
| 5,718,925 A | 2/1998 | Kristinsson et al. |
| 5,748,845 A | 5/1998 | Labun et al. |
| 5,776,205 A | 7/1998 | Phillips |
| 5,885,809 A | 3/1999 | Effenberger et al. |
| 5,888,212 A | 3/1999 | Petrofsky et al. |
| 5,888,213 A | 3/1999 | Scars et al. |
| 5,898,948 A | 5/1999 | Kelly et al. |
| 5,910,720 A | 6/1999 | Williamson et al. |
| 5,932,230 A | 8/1999 | DeGrate |
| 5,944,760 A | 8/1999 | Christensen |
| 5,971,729 A | 10/1999 | Kristinsson et al. |
| 5,972,036 A | 10/1999 | Kristinsson et al. |
| 5,980,435 A | 11/1999 | Joutras et al. |
| 6,029,374 A | 2/2000 | Herr et al. |
| 6,056,712 A | 5/2000 | Grim |
| 6,067,892 A | 5/2000 | Erickson |
| 6,071,313 A | 6/2000 | Phillips |
| 6,136,039 A | 10/2000 | Kristinsson et al. |
| 6,144,385 A | 11/2000 | Girard |
| 6,202,806 B1 | 3/2001 | Sandrin et al. |
| 6,223,648 B1 | 5/2001 | Erickson |
| 6,240,797 B1 | 6/2001 | Morishima et al. |
| 6,267,742 B1 | 7/2001 | Krivosha et al. |
| 6,416,703 B1 | 7/2002 | Kristinsson et al. |
| 6,443,993 B1 | 9/2002 | Koniuk |
| 6,456,884 B1 | 9/2002 | Kenney |
| 6,478,826 B1 | 11/2002 | Phillips et al. |
| 6,485,776 B2 | 11/2002 | Janusson et al. |
| 6,507,757 B1 | 1/2003 | Swain et al. |
| 6,511,512 B2 | 1/2003 | Phillips et al. |
| 6,517,503 B1 | 2/2003 | Naft et al. |
| 6,585,774 B2 | 7/2003 | Dean, Jr. et al. |
| 6,589,289 B2 | 7/2003 | Ingimarsson |
| 6,592,539 B1 | 7/2003 | Einarsson et al. |
| 6,610,101 B2 | 8/2003 | Herr et al. |
| 6,626,952 B2 | 9/2003 | Janusson et al. |
| 6,660,042 B1 | 12/2003 | Curcie et al. |
| 6,666,796 B1 | 12/2003 | MacCready |
| 6,706,364 B2 | 3/2004 | Janusson et al. |
| 6,752,774 B2 | 6/2004 | Townsend et al. |
| 6,764,520 B2 | 7/2004 | Deffenbaugh et al. |
| 6,811,571 B1 | 11/2004 | Phillips |
| D503,480 S | 3/2005 | Ingimundarson et al. |
| D503,802 S | 4/2005 | Bjarnason |
| 6,887,279 B2 | 5/2005 | Phillips et al. |
| 6,923,834 B2 | 8/2005 | Karason |
| 6,936,073 B2 | 8/2005 | Karason |
| 6,942,629 B2 | 9/2005 | Hepburn et al. |
| 6,945,947 B2 | 9/2005 | Ingimundarson et al. |
| 6,966,882 B2 | 11/2005 | Horst |
| 6,969,408 B2 | 11/2005 | Lecomte et al. |
| 7,001,563 B2 | 2/2006 | Janusson et al. |
| 7,025,793 B2 | 4/2006 | Egilsson |
| 7,029,500 B2 | 4/2006 | Martin |
| 7,037,283 B2 | 5/2006 | Karason et al. |
| D523,149 S | 6/2006 | Bjarnason |
| 7,063,727 B2 | 6/2006 | Phillips et al. |

| Patent | Type | Date | Inventor |
|---|---|---|---|
| 7,077,818 | B2 | 7/2006 | Ingimundarson et al. |
| 7,094,058 | B2 | 8/2006 | Einarsson |
| 7,094,212 | B2 | 8/2006 | Karason et al. |
| D527,825 | S | 9/2006 | Ingimundarson et al. |
| D529,180 | S | 9/2006 | Ingimundarson et al. |
| 7,101,487 | B2 | 9/2006 | Hsu et al. |
| 7,105,122 | B2 | 9/2006 | Karason |
| 7,107,180 | B2 | 9/2006 | Karason |
| 7,118,601 | B2 | 10/2006 | Yasui et al. |
| 7,118,602 | B2 | 10/2006 | Bjarnason |
| 7,136,722 | B2 | 11/2006 | Nakamura et al. |
| D533,280 | S | 12/2006 | Wyatt et al. |
| 7,144,429 | B2 | 12/2006 | Carstens |
| 7,145,305 | B2 | 12/2006 | Takenaka et al. |
| 7,154,017 | B2 | 12/2006 | Sigurjonsson et al. |
| 7,161,056 | B2 | 1/2007 | Gudnason et al. |
| 7,169,188 | B2 | 1/2007 | Carstens |
| 7,169,189 | B2 | 1/2007 | Bjarnason et al. |
| 7,169,190 | B2 | 1/2007 | Phillips et al. |
| 7,198,071 | B2 | 4/2007 | Bisbee et al. |
| 7,198,610 | B2 | 4/2007 | Ingimundarson et al. |
| 7,217,060 | B2 | 5/2007 | Ingimarsson |
| 7,220,889 | B2 | 5/2007 | Sigurjonsson et al. |
| 7,223,899 | B2 | 5/2007 | Sigurjonsson |
| 7,227,050 | B2 | 6/2007 | Sigurjonsson et al. |
| 7,230,154 | B2 | 6/2007 | Sigurjonsson |
| 7,235,108 | B2 | 6/2007 | Carstens |
| 7,240,876 | B2 | 7/2007 | Doubleday et al. |
| 7,266,910 | B2 | 9/2007 | Ingimundarson |
| 7,270,644 | B2 | 9/2007 | Ingimundarson |
| 7,279,009 | B2 | 10/2007 | Herr et al. |
| 7,288,076 | B2 | 10/2007 | Grim et al. |
| 7,295,892 | B2 | 11/2007 | Herr et al. |
| RE39,961 | E | 12/2007 | Petrofsky et al. |
| 7,303,538 | B2 | 12/2007 | Grim et al. |
| 7,304,202 | B2 | 12/2007 | Sigurjonsson et al. |
| 7,311,686 | B1 | 12/2007 | Iglesias et al. |
| 7,313,463 | B2 | 12/2007 | Herr et al. |
| D558,884 | S | 1/2008 | Ingimundarson et al. |
| 7,335,233 | B2 | 2/2008 | Hsu et al. |
| 7,347,877 | B2 | 3/2008 | Clausen et al. |
| D567,072 | S | 4/2008 | Ingimundarson et al. |
| 7,371,262 | B2 | 5/2008 | Lecomte et al. |
| 7,377,944 | B2 | 5/2008 | Janusson et al. |
| RE40,363 | E | 6/2008 | Grim et al. |
| 7,381,860 | B2 | 6/2008 | Gudnason et al. |
| 7,393,364 | B2 | 7/2008 | Martin |
| 7,396,975 | B2 | 7/2008 | Sigurjonsson et al. |
| 7,402,721 | B2 | 7/2008 | Sigurjonsson et al. |
| 7,411,109 | B2 | 8/2008 | Sigurjonsson et al. |
| D576,781 | S | 9/2008 | Chang et al. |
| D577,828 | S | 9/2008 | Ingimundarson et al. |
| 7,423,193 | B2 | 9/2008 | Sigurjonsson et al. |
| 7,427,297 | B2 | 9/2008 | Patterson et al. |
| 7,429,253 | B2 | 9/2008 | Shimada et al. |
| 7,431,708 | B2 | 10/2008 | Sreeramagiri |
| 7,431,737 | B2 | 10/2008 | Ragnarsdottir et al. |
| 7,438,843 | B2 | 10/2008 | Asgeirsson |
| 7,449,005 | B2 | 11/2008 | Pickering et al. |
| 7,455,696 | B2 | 11/2008 | Bisbee, III et al. |
| D583,956 | S | 12/2008 | Chang et al. |
| 7,459,598 | B2 | 12/2008 | Sigurjonsson et al. |
| 7,465,281 | B2 | 12/2008 | Grim et al. |
| 7,465,283 | B2 | 12/2008 | Grim et al. |
| 7,468,471 | B2 | 12/2008 | Sigurjonsson et al. |
| 7,470,830 | B2 | 12/2008 | Sigurjonsson et al. |
| 7,488,349 | B2 | 2/2009 | Einarsson |
| 7,488,864 | B2 | 2/2009 | Sigurjonsson et al. |
| D588,753 | S | 3/2009 | Ingimundarson et al. |
| 7,503,937 | B2 | 3/2009 | Asgeirsson et al. |
| 7,513,880 | B2 | 4/2009 | Ingimundarson et al. |
| 7,513,881 | B1 | 4/2009 | Grim et al. |
| D592,755 | S | 5/2009 | Chang et al. |
| D592,756 | S | 5/2009 | Chang et al. |
| 7,527,253 | B2 | 5/2009 | Sugar et al. |
| 7,531,006 | B2 | 5/2009 | Clausen et al. |
| 7,531,711 | B2 | 5/2009 | Sigurjonsson et al. |
| 7,534,220 | B2 | 5/2009 | Cormier et al. |
| 7,544,214 | B2 | 6/2009 | Gramnas |
| 7,549,970 | B2 | 6/2009 | Tweardy |
| D596,301 | S | 7/2009 | Campos et al. |
| 7,578,799 | B2 | 8/2009 | Thorsteinsson et al. |
| 7,581,454 | B2 | 9/2009 | Clausen et al. |
| 7,597,672 | B2 | 10/2009 | Kruijsen et al. |
| 7,597,674 | B2 | 10/2009 | Hu et al. |
| 7,597,675 | B2 | 10/2009 | Ingimundarson et al. |
| 7,618,463 | B2 | 11/2009 | Oddsson et al. |
| 7,632,315 | B2 | 12/2009 | Egilsson |
| 7,637,957 | B2 | 12/2009 | Ragnarsdottir et al. |
| 7,637,959 | B2 | 12/2009 | Clausen et al. |
| 7,641,700 | B2 | 1/2010 | Yasui |
| 7,650,204 | B2 | 1/2010 | Dariush |
| 7,662,191 | B2 | 2/2010 | Asgeirsson |
| D611,322 | S | 3/2010 | Robertson |
| 7,674,212 | B2 | 3/2010 | Kruijsen et al. |
| 7,691,154 | B2 | 4/2010 | Asgeirsson et al. |
| 7,696,400 | B2 | 4/2010 | Sigurjonsson et al. |
| 7,704,218 | B2 | 4/2010 | Einarsson et al. |
| D616,555 | S | 5/2010 | Thorgilsdottir et al. |
| D616,556 | S | 5/2010 | Hu |
| 7,713,225 | B2 | 5/2010 | Ingimundarson et al. |
| D616,996 | S | 6/2010 | Thorgilsdottir et al. |
| D616,997 | S | 6/2010 | Thorgilsdottir et al. |
| D618,359 | S | 6/2010 | Einarsson |
| 7,727,174 | B2 | 6/2010 | Chang et al. |
| 7,736,394 | B2 | 6/2010 | Bedard et al. |
| 7,745,682 | B2 | 6/2010 | Sigurjonsson et al. |
| D620,124 | S | 7/2010 | Einarsson |
| 7,749,183 | B2 | 7/2010 | Ingimundarson et al. |
| 7,749,281 | B2 | 7/2010 | Egilsson |
| 7,762,973 | B2 | 7/2010 | Einarsson et al. |
| 7,770,842 | B2 | 8/2010 | Benson |
| 7,771,488 | B2 | 8/2010 | Asgeirsson et al. |
| 7,780,741 | B2 | 8/2010 | Janusson et al. |
| 7,794,418 | B2 | 9/2010 | Ingimundarson et al. |
| 7,794,505 | B2 | 9/2010 | Clausen et al. |
| 7,811,333 | B2 | 10/2010 | Jonsson et al. |
| 7,811,334 | B2 | 10/2010 | Ragnarsdottir et al. |
| D627,079 | S | 11/2010 | Robertson |
| 7,833,181 | B2 | 11/2010 | Cormier et al. |
| 7,842,848 | B2 | 11/2010 | Janusson et al. |
| D628,696 | S | 12/2010 | Robertson |
| D629,115 | S | 12/2010 | Robertson |
| 7,846,213 | B2 | 12/2010 | Lecomte et al. |
| 7,862,620 | B2 | 1/2011 | Clausen et al. |
| 7,863,797 | B2 | 1/2011 | Calley |
| 7,867,182 | B2 | 1/2011 | Iglesias et al. |
| 7,867,284 | B2 | 1/2011 | Bedard |
| 7,867,285 | B2 | 1/2011 | Clausen et al. |
| 7,867,286 | B2 | 1/2011 | Einarsson |
| 7,868,511 | B2 | 1/2011 | Calley |
| 7,879,110 | B2 | 2/2011 | Phillips |
| 7,891,258 | B2 | 2/2011 | Clausen et al. |
| 7,892,195 | B2 | 2/2011 | Grim et al. |
| D634,438 | S | 3/2011 | Hu |
| D634,852 | S | 3/2011 | Hu |
| 7,896,826 | B2 | 3/2011 | Hu et al. |
| 7,896,827 | B2 | 3/2011 | Ingimundarson et al. |
| 7,896,927 | B2 | 3/2011 | Clausen et al. |
| 7,909,884 | B2 | 3/2011 | Egilsson et al. |
| 7,910,793 | B2 | 3/2011 | Sigurjonsson et al. |
| 7,914,475 | B2 | 3/2011 | Wyatt et al. |
| 7,918,765 | B2 | 4/2011 | Kruijsen et al. |
| D637,942 | S | 5/2011 | Lee et al. |
| 7,935,068 | B2 | 5/2011 | Einarsson |
| D640,380 | S | 6/2011 | Tweardy et al. |
| D640,381 | S | 6/2011 | Tweardy et al. |
| 7,959,589 | B2 | 6/2011 | Sreeramagiri et al. |
| D641,482 | S | 7/2011 | Robertson et al. |
| D641,483 | S | 7/2011 | Robertson et al. |
| 7,981,068 | B2 | 7/2011 | Thorgilsdottir et al. |
| 7,985,193 | B2 | 7/2011 | Thorsteinsson et al. |
| D643,537 | S | 8/2011 | Lee |
| 7,992,849 | B2 | 8/2011 | Sugar et al. |

| | | |
|---|---|---|
| 7,998,221 B2 | 8/2011 | Lecomte et al. |
| 8,002,724 B2 | 8/2011 | Hu et al. |
| 8,007,544 B2 | 8/2011 | Jonsson et al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 8,034,120 B2 | 10/2011 | Egilsson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| 8,048,007 B2 | 11/2011 | Roy |
| 8,048,013 B2 | 11/2011 | Ingimundarson et al. |
| 8,048,172 B2 | 11/2011 | Jonsson et al. |
| 8,052,760 B2 | 11/2011 | Egilsson et al. |
| 8,057,550 B2 | 11/2011 | Clausen et al. |
| 2001/0029400 A1 | 10/2001 | Deffenbaugh et al. |
| 2002/0052663 A1 | 5/2002 | Herr et al. |
| 2002/0092724 A1 | 7/2002 | Koleda |
| 2002/0138153 A1 | 9/2002 | Koniuk |
| 2003/0093021 A1 | 5/2003 | Goffer |
| 2003/0125814 A1 | 7/2003 | Paasivaara et al. |
| 2003/0139783 A1 | 7/2003 | Kilgore et al. |
| 2003/0163206 A1 | 8/2003 | Yasui et al. |
| 2003/0195439 A1 | 10/2003 | Caselnova |
| 2004/0039454 A1 | 2/2004 | Herr et al. |
| 2004/0049290 A1 | 3/2004 | Bedard |
| 2004/0054423 A1 | 3/2004 | Martin |
| 2004/0064195 A1 | 4/2004 | Herr |
| 2004/0088025 A1 | 5/2004 | Gesotti |
| 2004/0181118 A1 | 9/2004 | Kochamba |
| 2004/0181289 A1* | 9/2004 | Bedard et al. .................. 623/24 |
| 2005/0007834 A1 | 1/2005 | Hidaka |
| 2005/0043614 A1 | 2/2005 | Huizenga et al. |
| 2005/0049652 A1 | 3/2005 | Tong |
| 2005/0059908 A1 | 3/2005 | Bogert |
| 2005/0085948 A1 | 4/2005 | Herr et al. |
| 2005/0155444 A1 | 7/2005 | Otaki et al. |
| 2005/0209707 A1 | 9/2005 | Phillips et al. |
| 2005/0228515 A1 | 10/2005 | Musallam et al. |
| 2006/0004307 A1 | 1/2006 | Horst |
| 2006/0064047 A1 | 3/2006 | Shimada et al. |
| 2006/0069448 A1 | 3/2006 | Yasui |
| 2006/0094989 A1 | 5/2006 | Scott et al. |
| 2006/0213305 A1 | 9/2006 | Sugar et al. |
| 2006/0224246 A1 | 10/2006 | Clausen et al. |
| 2006/0249315 A1 | 11/2006 | Herr et al. |
| 2006/0258967 A1 | 11/2006 | Fujil et al. |
| 2006/0264790 A1 | 11/2006 | Kruijsen et al. |
| 2006/0276728 A1 | 12/2006 | Ashihara et al. |
| 2007/0016329 A1 | 1/2007 | Herr et al. |
| 2007/0043449 A1 | 2/2007 | Herr et al. |
| 2007/0050044 A1 | 3/2007 | Haynes et al. |
| 2007/0123997 A1 | 5/2007 | Herr et al. |
| 2007/0129653 A1 | 6/2007 | Sugar et al. |
| 2007/0162152 A1 | 7/2007 | Herr et al. |
| 2007/0267791 A1 | 11/2007 | Hollander et al. |
| 2008/0114272 A1 | 5/2008 | Herr et al. |
| 2008/0155444 A1 | 6/2008 | Pannese et al. |
| 2009/0030530 A1 | 1/2009 | Martin |
| 2009/0222105 A1 | 9/2009 | Clausen |
| 2011/0224804 A1 | 9/2011 | Clausen et al. |
| 2011/0245931 A1 | 10/2011 | Clausen et al. |
| 2011/0260380 A1 | 10/2011 | Hollander et al. |
| 2011/0264230 A1 | 10/2011 | Herr et al. |
| 2011/0278857 A1 | 11/2011 | Sugar et al. |
| 2012/0209405 A1 | 8/2012 | Herr et al. |
| 2012/0271433 A1 | 10/2012 | Galea et al. |

FOREIGN PATENT DOCUMENTS

| | | |
|---|---|---|
| EP | 1534117 | 6/2005 |
| WO | WO 03/068453 | 8/2003 |
| WO | WO 2004/017872 A1 | 3/2004 |
| WO | WO 2004/019832 A1 | 3/2004 |
| WO | WO 2010/027968 A2 | 3/2010 |

OTHER PUBLICATIONS

Herr, Hugh et al. "New Horizons for Orthotic and Prosthetic Technology: Artificial Muscle for Ambulation," The MIT Media Laboratory, pp. 1-9, 2004.

Williamson, Matthew M., "Series Elastic Actuators," MIT Artificial Intelligence Laboratory, Jan. 1995.

Au, S.K. et al., "Powered Ankle-Foot Prosthesis for the Improvement of Amputee Ambulation," paper presented at the Proceedings of the 29th Annual International Conference of the IEEE Eng. Med. Bio. Soc., Cité Internationale, Lyon, France, (Aug. 2007).

International Search Report and Written Opinion for corresponding International Application No. PCT/US2010/022783, Dated: May 4, 2010.

Blaya, J.A., "Force-Controllable Ankle Foot Orthosis (AFO) to Assist Drop Foot Gait," submitted to the Department of Mechanical Engineering, Massachusetts Institute of Technology, Cambridge, Massachusetts (Feb. 2003), 88 pages.

Blaya, J.A. et al., "Adaptive Control of a Variable-Impedance Ankle-Foot Orthosis to Assist Drop Foot Gait," Artificial Intelligence Lab and Harvard-MIT Division Health Sciences and Technology, Boston, MA, 30 pages.

Blaya, J.A. et al., "Active Ankle Foot Orthoses (AAFO)," Retrieved from: http://www.ai.mit.edu. Artificial Intelligence Laboratory, Massachusetts Institute of Technology, Cambridge, Massachusetts, 3 pages.

Dollar, et al., "Lower Extremity Exoskeletions and Active Orthoses: Challenges and State-of-the-Art," *IEEE Transcations on Robotics*, vol. 24, No. 1, Feb. 2008, 15 pages.

Drake, C., "Foot & Ankle Splints or Orthoses," HemiHelp Information Sheet, London, United Kingdom, 3 pages, http://www.hemihelp.org.uk/leaflets/hbleaflets90.htm Retrieved on: Jun. 20, 2003.

Hogan, N., "Impedance Control: An Approach to Manipulation," Dept. of Mechanical Engineering and Labortory of Manufacturing and Productivity, Massachusetts Institute of Technology, Cambridge MA, pp. 304-313 (Jun. 1984).

Hogan, N., "Impedance Control: An Approach to Manipulation: Part II—Implementation, " *Journal of Dynamic Systems, Measurement and Control, 107*: 8-16 (1985).

Hogan, N., "Impedance Control: An Approach to Manipulation: Part III—Application," *Journal of Dynamics Systems, Measurement and Control*, 107: 17-24 (1985).

Kim, J.-H. et al., "Realization of Dynamic Walking for the Humaniod Robot Platform KHR-1," *Advanced Robotics*, 18(7): 749-768, (2004).

Klute, G.K. el al., "Powering Lower Limb Prosthestics with Muscle-Like Actuators," Abstract in: Proceeding of the 1st Annual Meeting of the VA Rehabilitation Research and Development Service, "Enabling Veterans: Meeting the Challenge of Rehabilitation in the Next Millennium," Washington, D.C., p. 52 (Oct. 1998).

Klute, G.K. et al., "Artificial Muscles: Actuators for Biorobotic Systems," *The International Journal of Robotics Research*, 21(4): 295-309 (2002).

Klute, G.K. et al., "Artificial Muscles: Actuators for Lower Limb Prostheses," Abstract in: Proceedings of the 2nd Annual Meeting of the VA rehabilitation Research and Development Service, Feb. 20-22, 2000, p. 107.

Klute, G.K. et al., "Artificial Tendons: Biomechanical Design Properties for Prosthetic Lower Limbs," Chicago 2000 World Congress on Medical Physics and Biomedical Engineering, Chicago on Jul. 24-28, 2000, 4 pages.

Klute, G.K. et al., "Intelligent Transtibial Prostheses with Muscle-Like Actuators," 2002 American Physiological Society Intersociety Meeting: The Power of Comparative Physiology: Evolution, Integration, and Applied, 1 page.

Klute, G.K. et al., "Lower Limb Prostheses Powered by Muscle-Like Pneumatic Actuator," Submitted to Oleodinamica e Pneumatica, Publishe Tecniche Nuove, Milamo, Italy, Mar. 15, 2000, 6 pages.

Klute, G.K. et al., "McKibben Artificial Muscles: Pneumatic Actuators with Biomechanical Intelligence," IEEE/ASME 1999 International Conference on Advanced Intelligent Mechatronics, Atlanta, GA, pp. 221-226 (Sep. 1999).

Klute, G.K. et al., "Muscle-Like Pneumatic Actuators for Below-Knee Prostheses," Actuator 2000: 7th International Conference on New Actuators, Bremen, Germany on Jun. 9-21, 2000, pp. 289-292.

Klute, G.K. et al., "Variable Stiffness Prosthesis for Transtibial Amputees," Dept of Veteran Affairs, Seattle, WA USA, 2 pages.

International Search Report and Written Opinion for International Application No. PCT/US2009/055600, Mailed: Apr. 29, 2010 (23 pages).

International Search Report and Written Opinion for International Application No. PCT/US2010/047279, Mailed: Jan. 19, 2011 (11 pages).

International Search Report and Written Opinion for International Application No. PCT/US2011/031105, Mailed: Oct. 11, 2011 (16 pages).

J. Hitt et al., "The Sparky (Spring Ankle with Regenerative Kinetics) Projects: Design and Analysis of a Robotic Transtibial prosthesis with Regenerative Kinetics," in Proc. IEEE Int. Conf. Robot. Autom., Orlando, Fla., pp. 2939-2945, May 2006.

Sup, F. et al., "Design and Control of a Powered Transfemoral Prosthesis," *The International Journal of Robotics Research*, vol. 27, No. 2, pp. 263-273 (2008).

Geyer, H. et al., "A Muscle-Reflex Model That Encodes Principles of Legged Mechanics Predicts Human Walking Dynamics and Muscle Activities," *IEEE Transactions on Neural Systems and Rehabilitation Engineering*, vol. 18, No. 3, pp. 263-273 (Jun. 2010).

Geyer, H. et al., "Positive Force Feedback in Bouncing Gaits?," *Proc. R Society. Lond. B*, 270, pp. 2173-2183 (2003).

Abbas, J.J. et al., "Neural Network Control of Functional Neuromuscular Stimulation Systems: Computer Simulation Studies," *IEEE Transactions on Biomedical Engineering*, vol. 42, No. 11, Nov. 1995, pp. 1117-1127.

Abul-Haj, C.J. et al., "Functional Assessment of Control Systems for Cybernetic Elbow Prostheses—Part II: Application of the Technique," *IEEE Transactions on Biomedical Engineering*, vol. 17, No. 11, Nov. 1990, pp. 1037-1047.

Akazawa, K. et al., "Biomimetic EMG-Prosthesis-Hand, 18$^{th}$ Annual International Conference of the IEEE Engineering in Medicine and Biology Society," Amsterdam 1996, pp. 535 and 536.

Aminian, K. et al., "Estimation of Speed and Incline of Walking Using Neural Network," *IEEE Transactions of Instrumentation and Measurement*, 44(3): 743-746 (1995).

Anderson, F.C. et al., "Dynamic Optimization of Human Walking," *Journal of Biomechanical Engineering*, 123: 381-390 (2001).

Andrews, B.J. et al., "Hybrid FES Orthosis Incorporating Closed Loop Control and Sensory Feedback," *J. Biomed. Eng.*, 10: 189-195(1988).

Au, S.K. et al., "An Ankle-Foot Emulation System for the Study of Human Walking Biomechanics," Proceedings of the 2006 IEEE International Conference on Robotics and Automation, Orlando, FLA, May 2006, pp. 2939-2945.

Au, S.K. et al., "Biomechanical Design of a Powered Ankle-Foot Prosthesis," Proceedings of the 2007 IEEE 10$^{th}$ International Conference on Rehabilitation Robotics, Noordwijk, The Netherlands, Jun. 12-15, pp. 298-303.

Au, S.K. et al., "An EMG-Position Controlled System for an Active Ankle-Foot Prosthesis: An Initial Experimental Study," Proceedings of the 2005 IEEE 9$^{th}$ International Conference on Rehabilitation Robotics, Chicago, IL., pp. 375-379.

Au, S.K. et al., "Initial Experimental Study on Dynamic Interaction Between an Amputee and a Powered Ankle-Foot Prostheses," Harvard-MIT Division of Health Sciences and Technology, MIT, Cambridge, MA.

Arakawa, T. et al., "Natural Motion Generation of Biped Locomotion Robot Using Hierarchical Trajectory Generation Method Consisting of GA, EP Layers," Proceedings of the 1997 IEEE International Conference on Robotics and Automation, Albuquerque, NM., pp. 375-379.

Au, S.K. et al., "Powered Ankle-Foot Prosthesis Improves Walking Metabolic Economy," *IEEE Transactions on Robotics*, 25(1): 51-66 (2009).

Au, S.K. et al., "Powered Ankle-Foot Prosthesis for the Improvement of Amputee Ambulation," paper presented at the Proceedings of the 29$^{th}$ Annual International Conference of the IEEE EMBS Cité Internationale, Lyon, France, (Aug. 2007).

Au, S. et al., "Powered Ankle-Foot Prosthesis to Assist Level-Ground and Stair-Descent Gaits," *Neural Networks*, 21: 654-666 (2008).

Barth, D.G. et al., "Gait Analysis and Energy Cost of Below-Knee Amputees Wearing Six Different Prosthetic Feet," *JPO*, 4(2): 63 (1992).

Bateni, H. et al., "Kinematic and Kinetic Variations of Below-Knee Amputee Gait," *JPO*, 14(1):1-12 (2002).

Baten, Chris T.M. et al., "Inertial Sensing in Ambulatory Back Load Estimation," paper presented at the 18$^{th}$ Annual International Conference of the IEEE Engineering in Medicine and Biology Society, Amsterdam, 1996, pp. 497-498.

Blaya, J. et al., "Active Ankle Foot Orthoses (AAFO)," Artificial Intelligence Laboratory, Massachusetts Institute of Technology, Cambridge, MA, pp. 275-277.

Blaya, J.A. et al., "Adaptive Control of a Variable-Impedance Ankle-Foot Orthosis to Assist Drop-Foot Gait," IEEE Transactions on Neural Systems and Rehabilitation Engineering, 12(1): 24-31 (2004).

Blaya, J.A. et al., "Force-Controllable Ankle-Foot Orthosis (AFO) to Assist Drop Foot Gait," Massachusetts Institute of Technology, Feb. 2003, pp. 1-96.

Blickhan, R., "The Spring-Mass Model for Running and Hopping," *J. Biomechanics*, 22(11 /12): 1217-1227 (1989).

Bortz, J.E. "A New Mathematical Formulation for Strapdown Inertial Navigation," *IEEE Transactions on Aerospace and Electronic Systems*, AES-7(1): 61-66 (1971).

Bouten, C.V. et al., "Assessment of Energy Expenditure for Physical Activity Using a Triaxial Accelerometer," *Medicine and Science in Sports and Exercise*, pp. 1516-1523.

Brockway, J.M., "Derivation of Formulae Used to Calculate Energy Expenditure in Man," *Human Nutrition: Clinical Nutrition* (1987), 41C, pp. 463-471.

Brown, T. Graham, "On the Nature of the Fundamental Activity of the Nervous Centres; Together with an Analysis of the Conditioning of Rhythmic Activity in Progression, and a Theory of the Evolution of Function in the Nervous System," pp. 24-46.

AJG The American Journal of Gastroenterology, "Symptoms Diagnosis," 105(4): 1-875 (2010).

Chu, A. et al., "On the Biomimetic Design of the Berkeley Lower Extremity Exoskeleton," paper presented at the Proceedings of the 2005 IEEE International Conference on Robotics and Automation, Barcelona, Spain, (Apr. 2005) pp. 4556-4363.

American Journal of Physical Medicine & Rehabilitation, 71(5): 1-278 (1992).

Colgate, James Edward, "The Control of Dynamically Interacting Systems," Massachusetts Institute of Technology, Aug. 1988, pp. 1-15.

Collins, S.H. et al., "Controlled Energy Storage and Return Prosthesis Reduces Metabolic Cost of Walking," ISB XXth Congress—ASB 29$^{th}$ Annual Meeting, Jul. 31-Aug. 5, Cleveland, Ohio, pp. 804.

Collins, S.H. et al., "Efficient Bipedal Robots Based on Passive-Dynamic Walkers," Feb. 11, 2005, pp. 1-8.

Crago, P.E. et al., "New Control Strategies for Neuroprosthetic Systems," *Journal of Rehabilitation Research and Development*, vol. 33, No. 2, Apr. 1996, pp. 158-172.

Daley, M.A. et al., "Running Stability is Enhanced by a Proximo-Distal Gradient in Joint Neuromechanical Control," *The Journal of Experimental Biology*, vol. 210, pp. 383-394 (Feb. 2007).

Dapena, J. et al., "A Three-Dimensional Analysis of Angular Momentum in the Hammer Throw," Biomechanics Laboratory, Indiana University, IN, *Medicine and Science in Sports and Exercise*, vol. 21, No. 2, pp. 206-220 (1988).

Dietz, V. "Proprioception and Locomotor Disorders," *Nature Reviews*, vol. 3, pp. 781-790 (Oct. 2002).

Dietz, V. "Spinal Cord Pattern Generators for Locomotion," *Clinical Neurophysiology*, vol. 114, Issue 8, pp. 1-12 (Aug. 2003).

Doerschuk, P.C. et al., "Upper Extremity Limb Function Discrimination Using EMG Signal Analysis," *IEEE Transactions on Biomedical Engineering*, vol. BME-30, No. 1, Jan. 1983, pp. 18-28.

Doke, J. et al., "Mechanics and Energetics of Swinging the Human Leg," *The Journal of Experimental Biology*, vol. 208, pp. 439-445 (2005).

Dollar, A.M. et al., "Lower Extremity Exoskeletons and Active Orthoses: Challenges and State-of-the-Art," *IEEE Transactions on Robotics*, vol. 24, No. 1, Feb. 2008, pp. 1-15.

Donelan, J.M. et al., "Force Regulation of Ankle Extensor Muscle Activity in Freely Walking Cats," *Journal of Neurophysiology*, vol. 101, pp. 360-371 (2009).

Donelan, J.M. et al., "Mechanical work for Step-to-Step Transitions is a Major Determinant of the Metabolic Cost of Human Walking," *The Journal of Experimental Biology*, vol. 205, pp. 3717-3727 (2002).

Donelan, J.M. et al., "Simultaneous Positive and Negative External Mechanical Work in Human Walking," *Journal of Biomechanics*, vol. 35, 2002, pp. 117-124 (2002).

HemiHelp, "Ankle & Foot Splints or Orthoses," (AFOs).

HemiHelp, "Foot & Ankle Splints or Orthoses," pp. 1-5.

Drake, C., "Foot & Ankle Splints or Orthoses," pp. 1-3.

Eilenberg, M.F. "A Neuromuscular-Model Based Control Strategy for Powered Ankle-Foot Prostheses," Massachusetts Institute of Technology, pp. 1-90.

Ekeberg, Ö et al., "Computer Simulation of Stepping in the Hind Legs of the Cat: An Examination of Mechanisms Regulating the Stance-to-Swing Transition," *J. Neurophysical*, vol. 94, pp. 4256-4268 (2005).

Ekeberg, Ö et al., "Simulations of Neuromuscular Control in Lamprey Swimming," The Royal Society, *Phil. Trans. R. Soc. Land*, vol. 354, pp. 895-902 (1999).

Endo, K. et al., "A Quasi-Passive Model of Human Leg Function in Level-Ground Walking," Proceedings of the 2006 IEEE/RSJ International Conference on Intelligent Robots and Systems, Oct. 9-15, 2006, Beijing, China, pp. 4935-4939.

Eppinger, S.D. et al., "Three Dynamic Problems in Robot Force Control," *IEEE Transactions on Robotics and Automation*, vol. 8, No. 6, pp. 772-778 (Dec. 1992).

Esquenazi, A. et al., "Rehabilitation After Amputation," vol. 91, No. 1, pp. 1-22 (Jan. 2001).

Farley, C.T. et al., "Energetics of Walking and Running: Insights From Simulated Reduced-Gravity Experiments," Harvard University, pp. 2709-2712.

Farry, K.A. et al., "Myoelectric Teleoperation of a Complex Robotic Hand," *IEEE Transactions on Robotics and Automation*, vol. 12, No. 5, pp. 775-778 (Oct. 1996).

Featherstone, R., "Robot Dynamics Algorithms," Edinburgh University, pp. 1-173.

Fite, K. et al., "Design and Control of an Electrically Powered Knee Prosthesis," Proceedings of the 2007 IEEE 10$^{th}$ International Conference on Rehabilitation Robotics, Jun. 12-15, The Netherlands, pp. 902-905.

Flowers, W.C., "A Man-Interactive Simulator System for Above-Knee Prosthetics Studies," MIT, pp. 1-94.

Fod, A. et al., "Automated Derivation of Primitives for Movement Classification," *Autonomous Robots*, vol. 12, No. 1, pp. 39-54 (Jan. 2002).

Frigon, A. et al., "Experiments and Models of Sensorimotor Interactions During Locomotion," *Biological Cybernetics*, vol. 95, pp. 606-627 (2006).

Fujita et al., "Joint Angle Control with Command Filter for Human Ankle Movement Using Functional Electrical Stimulation," IEEE Ninth Annual Conference of the Engineering in Medicine and Biology Society.

Fukuda, O. et al., "A Human-Assisting Manipulator Teleoperated by EMG Signals and Arm Motions," *IEEE Transactions on Robotics and Automation*, vol. 19, No. 2, pp. 210-222 (Apr. 2003).

Gates, D.H. Thesis: "Characterizing Ankle Function During Stair Ascent, Descent, and Level Walking for Ankle Prosthesis and Orthosis Design," Boston University, pp. 1-84.

Gerritsen, K.G.M. et al., "Direct Dynamics Simulation of the Impact Phase in Heel-Toe Running," *J. Biomechanics*, vol. 28, No. 6, pp. 661-668 (1995).

Geyer, H. et al., "A Muscle-Reflex Model that Encodes Principles of Legged Mechanics Produces Human Walking Dynamics and Muscle Activities," IEEE Transactions on Neural Systems and Rehabilitation Engineering, vol. X, No. X, pp. 1-10 (Date not provided).

Geyer, H. et al., "Compliant Leg Behavior Explains Basic Dynamics of Walking and Running," *Proc. R. Soc. B*, vol. 273, pp. 2861-2867 (2006).

Geyer, H. et al., "Positive Force Feedback in Bouncing Gaits?," *Proc. R. Soc. Lond, B*, vol. 270, pp. 2173-2183 (2003).

Ghigliazza, R.M. et al., "A Simply Stabilized Running Model," University of Pennsylvania, *SIAM Journal on Applied Dynamical Systems*, vol. 2, Issue 2, pp. 187-218 (May 8, 2004).

Giszter, S., et al., "Convergent Force Fields Organized in the Frog's Spinal Cord," *Journal of Neuroscience*, 13(2): 467-491 (1993).

Godha, S. et al., "Integrated GPS/INS System for Pedestrian Navigation in a Signal Degraded Environment," University of Calgary, Canada, pp. 1-14.

Goswami, A., "Postural Stability of Biped Robots and the Foot-Rotation Indicator (FRI) Point," *The International Journal of Robotics Research*, vol. 18, No. 6, pp. 523-533 (Jun. 1999).

Goswami, A. et al., "Rate of Change of Angular Momentum and Balance Maintenance of Biped Robots," Proceedings of the 2004 IEEE International Conference on Robotics and Automation, New Orleans, LA, Apr. 2004, pp. 3785-3790.

Graupe, D. et al., "A Microprocessor System for Multifunctional Control of Upper-Limb Prostheses via Myoelectric Signal Identification," *IEEE Transactions on Automatic Control*, vol. 23, No. 4, pp. 538-544 (Aug. 1978).

Gregoire, L. et al., "Role of Mono- and Biarticular Muscles in Explosive Movements," *International Journal of Sports Medicine*, vol. 5, No. 6, pp. 299-352 (Dec. 1984).

Grillner, S. and Zangger, P., "On the Central Generation of Locomotion in the Low Spinal Cat," *Experimental Brain Research*, 34: 241-261 (1979).

Grimes, D.L., "An Active Multi-Mode Above-Knee Prosthesis Controller," unpublished doctoral dissertation, Massachusetts Institute of Technology (1979).

Gunther, M. et al., "Human Leg Design: Optimal Axial Alignment Under Constraints," *J. Math. Biol.*, 48: 623-646 (2004).

Günther, M., and Ruder, H., "Synthesis of Two-Dimensional Human Walking: a test of the λ-model," *Biol. Cybern.*, 89: 89-106 (2003).

Gu, W.J., "The Regulation of Angular Momentum During Human Walking," unpublished doctoral dissertation, Massachusetts Institute of Technology (2003).

Brady, M. et al., "Robot Motion: Planning and Control," The MIT Press, Cambridge (1982).

Hansen, A.H., et al., "The Human Ankle During Walking: Implications for Design of Biomimetic Ankle Prostheses," *Journal of Biomechanics*, 37: 1467-1474 (2004).

Hayes, W.C., et al., "Leg Motion Analysis During Gait by Multiaxial Accelerometry: Theoretical Foundations and Preliminary Validations," *Journal of Biomechanical Engineering*, 105: 283-289 (1983).

Heglund, N. et al., "A Simple Design for a Force-Plate to Measure Ground Reaction Forces," *J. Exp. Biol.*, 93: 333-338 (1981).

Herr, H.M. et al., "A Model of Scale Effects in mammalian Quadrupedal Running," *The Journal of Experimental Biology*, 205: 959-967 (2002).

Herr, H.M., and Popovic, M., "Angular Momentum in Human Walking," *The Journal of Experimental Biology*, 211: 467-481 (2008).

Herr, H.M., and McMahon, T.A., "A Trotting Horse Model," *The International Journal of Robotics Research*, 19: 566-581 (2000).

Herr, H.M., and Wilkenfeld, A., "User-adaptive Control of a Magnetorheological Prosthetic Knee," *Industrial Robot: An International Journal*. 30(1): 42-55 (2003).

Heyn, A., et al., "The Kinematics of the Swing Phase Obtained From Accelerometer and Gyroscope Measurements," paper presented at the 18$^{th}$ Annual International Conference of the IEEE Engineering in Medicine and Biology Society, Amsterdam (1996).

Hill, A.V., "The Heat of Shortening and the Dynamic Constants of Muscle," *Proc. R. Soc. Lond.*, 126: 136-195 (1938).

Hirai, K., et al., "The Development of Honda Humanoid Robot," paper presented at the 1998 IEEE International Conference on Robotics & Automation (1998).

Hitt, J.K., et al., "The Sparky (Spring Ankle with Regenerative Kinetics) Project: Design and Analysis of a Robotic Transtibial Prosthesis with Regenerative Kinetics," Proceedings of the ASME International Design Engineering Technical Conferences and Computers and Information in Engineering Conference, Las Vegas, Nevada (2007).

Hofbaur, M.W., et al., "Hybrid Diagnosis with Unknown Behavioral Modes," Proceedings of the 13th International Workshop on Principles of Diagnosis (DX02) (2002).

Hofbaur, M.W., and Williams, B.C., "Mode Estimation of Probabilistic Hybrid Systems," MIT Space Systems and Artificial Intelligence Laboratories and Graz University of Technology, Department of Automatic Control.

Hof, A.L., et al., "Calf Muscle Moment, Work and Efficiency in Level Walking: Role of Series Elasticity," *J. Biochem.*, 16: 523-537 (1983).

Hofmann, A., et al., "A Sliding Controller for Bipedal Balancing Using Integrated Movement of Contact and Non-Contact Limbs," Proceedings of the 2004 IEEE/RSJ International Conference on Intelligence Robots and Systems, Japan (2004).

Hofmann, A.G., "Robust Execution of Bipedal Walking Tasks From Biomechanical Principles," unpublished doctoral dissertation for Massachusetts Institute of Technology (2006).

Hogan, N., "A Review of the Methods of Processing EMG for Use As a Proportional Control Signal," *Biomedical Engineering*, 11(3): 81-86 (1976).

Hogan, N., "Impedance Control—An Approach to Manipulation," unpublished doctoral dissertation for Department of Mechanical Engineering and Laboratory of Manufacturing and Productivity, Massachusetts Institute of Technology, pp. 304-313.

Hogan, N., and Buerger, S.P., "Impedance and Interaction Control, Robots and Automation Handbook."

Hogan, N., "Impedance Control: An Approach to Manipulation, Part III—Applications," *Journal of Dynamic Systems, Measurement, and Control*, 107: 17-24 (1985).

Hogan, N., "Impedance Control: An Approach to Manipulation: Part II—Implementation, " *Journal of Dynamic Systems, Measurement, and Control*,107: 8-16 (1985).

Hogan, N., "Impedance Control: An Approach to Manipulation: Part I—Theory," *Journal of Dynamic Systems, Measurement, and Control*, 107: 1-7 (1985).

Hollander, K.W. et al., "Adjustable Robotic Tendon using a 'Jack Spring'™," Proceedings of the 2005 IEEE, 9th International Conference on Rehabilitation Robotics, Jun. 28-Jul. 1, 2005, Chicago, IL, USA, pp. 113-118.

Howard, R.D., Thesis: "Joint and Actuator Design for Enhanced Stability in Robotic Force Control," Submitted to the Dept. of Aeronautics and Astronautics on Aug. 8, 1990 in partial fulfillment of the requirements for the degree of Doctor of Philosophy.

Huang, H.-P. et al., "Development of a Myoelectric Discrimination System for a Multi-Degree Prosthetic Hand," Proceedings of the 1999 IEEE, International Conference on Robotics & Automation, Detroit, Michigan, (1999).

Huang, Q. et al., "Planning Walking Patterns for a Biped Robot," *IEEE Transactions on Robotics and Automation*,17(3): 280-289 (Jun. 2001).

Hultborn, H., "Spinal reflexes, mechanisms and concepts: From Eccles to Lundberg and beyond," *Progress in Neurobiology*,78: 215-232 (2006).

Ijspeert, A.J., "Central pattern generators for locomotion control in animals and robots: a review," *Preprint of Neural Networks*, vol. 21, No. 4, pp. 642-653 (2008).

Ijspert, A.J. et al., "From swimming to walking with a salamander robot driven by a spinal cord model," pp. 1-5.

Ivashko, D.G. et al., "Modeling the spinal cord neural circuitry controlling cat hindlimb movement during locomotion," *Neurocomputing*, 52-54, pp. 621-629 (2003).

International Search Report and Written Opinion for International Application No. PCT/US2009/055600, Mailed: Apr. 29, 2010.

International Preliminary Report on Patentability for International Application No. PCT/US2010/047279; Mailed: Mar. 15, 2012.

International Search Report and Written Opinion for International Application No. PCT/US2010/047279; Mailed: Jan. 19, 2011.

International Search Report and Written Opinion for International Application No. PCT/US2011/031105, Mailed: Oct. 11, 2011.

Johansson, J.L. et al., "A Clinical Comparison of Variable-Damping and Mechanically Passive Prosthetic Knee Devices," Variable-Damping vs. Mechanically Passive Prosthetic Knees, Aug. 2005.

Johnson, C.T. et al., "Experimental Identification of Friction and Its Compensation in Precise, Position Controlled Mechanisms," *IEEE Transactions on Industry Applications*, vol. 28, No. 6, pp. 1392-1398 (Nov./Dec. 1992).

Jonic, S. et al., "Three Machine Learning Techniques for Automatic Determination of Rules to Control Locomotion," *IEEE Transactions on Biomedical Engineering*, vol. 46, No. 3, pp. 300-310 (Mar. 1999).

Kadaba, M.P. et al., "Measurement of Lower Extremity Kinematics During Level Walking," *Journal of Orthapedic Research*, pp. 383-392, 1990.

Kadaba, M.P. et al., "Repeatability of Kinematic, Kinetic, and Electromyographic Data in Normal Adult Gait," *Journal of Orthapedic Research*, pp. 849-860, 1989.

Kajita, S. et al., "A Hop towards Running Humanoid Biped," Proceedings of the 2004 IEEE International Conference on Robotics & Automation, pp. 629-635, 2004.

Kajita, S. et al., "Biped Walking on a Low Friction Floor," Proceedings of the 2004 IEEE/RSJ International Conference on Intelligent Robots & Systems, pp. 3546-3552, Sep. 28-Oct. 2, 2004, Sendai, Japan.

Kajita, S. et al., "Resolved Momentum Control: Humanoid Motion Planning based on the Linear and Angular Momentum," Proceedings of the 2003 IEEE/RSJ International Conference on Intelligent Robots & Systems, pp. 1644-1650 (2003).

Kaneko, K. et al., "Humanoid Robot HRP-2," Proceedings of the 2004 IEEE International Conference on Robotics & Automation, pp. 1083-1090 (Apr. 2004).

Kapti, A.O. et al., "Design and control of an active artificial knee joint," *Mechanism and Machine Theory*, vol. 41, pp. 1477-1485 (2006).

Katie, D. et al., "Survey of Intelligent Control Techniques for Humanoid Robots," *Journal of Intelligent and Robotic Systems*, vol. 37, pp. 117-141 (2003).

Kerrigan, D.C. et al., "A refined view of the determinants of gait: Significance of heel," *Archives of Physical Medicine and Rehabilitation*, vol. 81, Issue 8, pp. 1077-1080 (Aug. 2000).

Kerrigan, D.C. et al., "Quantification of pelvic rotation as a determinant of gait," Archives of Physical Medicine and Rehabilitation, vol. 82, Issue 2, pp. 217-220 (Feb. 2001).

Khatib, O. et al., "Coordination and Decentralized Cooperation of Multiple Mobile Manipulators," *Journal of Robotic Systems*, 13(11): 755-764 (1996).

Khatib, O. et al., "Whole-Body Dynamic Behavior and Control of Human-Like Robots," *International Journal of Humanoid Robotics*, vol. 1, No. 1, pp. 29-43 (2004).

Kidder, S.M. et al., "A System for the Analysis of Foot and Ankle Kinematics During Gait," *IEEE Transactions on Rehabilitation Engineering*, vol. 4, No. 1, pp. 25-32 (Mar. 1996).

Kim, J.-H. et al., "Realization of dynamic walking for the humanoid robot platform KHR-1," *Advanced Robotics*, vol. 18, No. 7, pp. 749-768 (2004).

Kirkwood, C.A. et al., "Automatic detection of gait events: a case study using inductive learning techniques," *J. Biomed. Eng.*, vol. 11, pp. 511-516 (Nov. 1989).

Kitayama, I. et al., "A Microcomputer Controlled Intelligent A/K Prosthesis—Fundamental Development," Proceedings, Seventh World Congress of ISPO, Jun. 28-Jul. 3, 1992, Chicago, Illinois, USA, 25 pages.

Klute, G.K. et al., "Artificial Muscles: Actuators for Lower Limb Prostheses," Abstract in: Proceedings of the 2nd Annual Meeting of the V A Rehabilitation Research and Development Service, Washington, D.C., Feb. 20-22, 2000, p. 107.

Klute, G.K. et al., "Artificial Muscles: Actuators for Biorobotic Systems," *The International Journal of Robotics Research*, vol. 21, pp. 295-309 (2002).

Klute, G.K. et al., "Artificial Muscles: Biomechanical Design Properties for Prosthetic Lower Limbs," Chicago 2000 World Congress on Medical Physics and Biomedical Engineering, Chicago on Jul. 24-28, 2000, 4 pages.

Klute, G.K. et al, "Intelligent transtibial prostheses with muscle-like actuators," 2002 American Physiological Society Intersociety Meeting: The Power of Comparative Physiology: Evolution, Integration, and Applied, 1 page abstract.

Klute, G.K. et al., "Lower Limb Prostheses Powered by Muscle-like Pneumatic Actuators," Submitted to Oleodinamica e Pneumatica, Publisher Tecniche Nuove, Milano, Italy, Mar. 15, 2000, pp. 1-6.

Klute, G.K. et al., "McKibben Artificial Muscles: Pneumatic Actuators with Biomechanical Intelligence," IEEE/ASME 1999 International Conference on Advanced Intelligent Mechatronics (AIM '99), Atlanta, GA, Sep. 19-22, 1999, pp. 221-226.

Klute, G.K. et al., "Mechanical properties of prosthetic limbs: Adapting to the patient," *Journal of Rehabilitation Research and Development*, vol. 38, No. 3, pp. 299-307 (May/Jun. 2001).

Klute, G.K. et al., "Muscle-like Pneumatic Actuators for Below-knee Prostheses," "Actuator 2000: $7^{th}$ International Conference on New Actuators," Bremen, Germany on Jun. 19-21, 2000, pp. 289-292.

Klute, G.K. et al., "Powering Lower Limb Prosthetics with Muscle-like Actuators," Abstract in: Proceedings of the $1^{st}$ Annual Meeting of the VA Rehabilitation Research and Development Service, "Enabling Veterans: Meeting the Challenge of Rehabilitation in the Next Millenium," Washington, D.C., Oct. 1-3, 1998, p. 52.

Klute, G.K. et al., "Variable Stiffness Prosthesis for Transtibial Amputees," 2 pages.

Koganezawa, K. et al., *Biomedical Engineering 1987*, 2.3: Control Aspects of Artificial Leg, pp. 71-85.

Kondak, K. et al., "Control and Online Computation of Stable Movement for Biped Robots," Proceedings of the 2003 IEEE/RSJ, Int'l Conference on Intelligent Robots and Systems, Las Vegas, Nevada, Oct. 2003, pp. 874-879.

Kostov, A. et al., "Machine Learning in Control of Functional Electrical Stimulation Systems for Locomotion," *IEEE Transactions on Biomedical Engineering*, vol. 42, No. 6, pp. 541-551 (Jun. 1995).

Kuo, A.D., "A Simple Model of Bipedal Walking Predicts the Preferred Speed-Step Length Relationship," *Transactions of the ASME*, vol. 123, pp. 264-269 (Jun. 2001).

Kuo, A.D., "Energetics of Actively Powered Locomotion Using the Simplest Walking Model," *Journal of Biomechanical Engineering*, vol. 124, pp. 113-120 (Feb. 2002).

Lafortune, M.A., "Three-Dimensional Acceleration of the Tibia During Walking and Running," *J. Biomechanics*, vol. 24, No. 10, pp. 877-886 (1991).

LeBlanc, M.K. et al., "Generation and Transfer of Angular Momentum in the Javelin Throw," American Society of Biomechanics, Presented at the $20^{th}$ Annual Meeting of the American Society of Biomechanics, Atlanta, Georgia, Oct. 17-19, 1996, 4 pages.

Light, L.H. et al., "Skeletal Transients on Heel Strike in Normal Walking with Different Footwear," *J. Biomechanics*, vol. 13, pp. 477-480 (1980).

Li, C. et al., "Research and Development of the Intelligently-Controlled Prosthetic Ankle Joint," Proceedings of the 2006 IEEE International Conference on Mechatronics and Automation, Jun. 25-28, 2006, Luoyana, China, pp. 1114-1119.

Liu, X. et al., "Development of a Lower Extremity Exoskeleton for Human Performance Enhancement," Proceedings of 2004 IEEE/RSJ International Conference on Intelligent Robots and Systems, Sep. 28-Oct. 2, 2004, Sendai, Japan, 3889-3894.

Lloyd, R. et al., "Kinetic changes associated with load carriage using two rucksack designs," *Ergonomics*, vol. 43, No. 9, pp. 1331-1341 (2000).

Luinge, H.J., *Inertial Sensing of Human Movement*, Twente University Press, Enschede, the Netherlands, 80 pages (Feb. 15, 1973).

Lundberg, A., "Reflex control of stepping," The Norwegian Academy of Science and Letters, The Nansen Memorial Lecture, Oct. 10, 1968, 40 pages.

Macfarlane, P.A. et al., "Gait Comparisons for Below-Knee Amputees Using a Flex-Foot(TM) Versus a Conventional Prosthetic Foot," JPO 1991, vol. 3, No. 4, pp. 150, htt://www.oandp.org/jpo/library/printArticle.asp?printArticleId=1991_04_150, Retrieved on: Feb. 9, 2012, 10 pages.

Maganaris, C.N., "Force-length characteristics of in vivo human skeletal muscle," *Acta Physiol Scand*, 172: 279-285 (2001).

Maganaris, C.N., "Force-Length Characteristics of the In Vivo Human Gastroenemius Muscle," *Clinical Anatomy*, 16: 215-223 (2003).

Martens, W.L. J., "Exploring the Information Content and Some Applications of Body Mounted Piezo-Resistive Accelerometers," 3 pages.

Maufroy, C. et al., "Towards a general neural controller for quadrupedal locomotion," Neural Networks, 21: 667-681 (2008).

Mayagoitia, R.E. et al., "Accelerometer and rate gyroscope measurement of kinematics: an inexpensive alternative to optical motion analysis systems," *Journal of Biomechanics*, 35: 537-542 (2002).

McFadyen, B.J. et al., "An Integrated Biomechanical Analysis of Normal Stair Ascent and Descent," J. Biomechanics, vol. 21, No. 9, pp. 733-744 (1988).

McGeer, T., "Passive Dynamic Walking," The International Journal of Robotics Research, 9, pp. 62-88 (1990).

McGreer, T., Chapter 4: "Principles of Walking and Running," *Advances in Comparative and Environmental Physiology*, vol. 11, pp. 113-139 (1992).

McIntosh, A.S. et al., "Gait dynamics on an inclined walkway," Journal of Biomechanics, vol. 39, Issue 13, pp. 2491-2502 (2006).

McMahon, T.A. et al., "Groucho Running," pp. 2326-2337 (1987).

McMahon, T.A. et al., "The Mechanics of Running: How Does Stiffness Couple with Speed?" J. Biomechanics, vol. 23, Suppl. 1, pp. 65-78 (1990).

Minassian, K. et al., "Human lumbar cord circuitries can be activated by extrinsic tonic input to generate locomotor-like activity," Human Movement Science, 26: 275-295 (2007).

Mochon, S. et al., "Ballistic Walking," *J. Biomechanics*, vol. 13, pp. 49-57 (1980).

Molen, N.H., "Energy/Speed Relation of Below-Knee Amputees Walking on a Motor-Driven Treadmill," Physiol, 31: 173-185 (1973).

Morris, J.R.W., "Accelerometry—A Technique for the Measurement of Human Body Movements," J. Biomechanics, vol. 6, pp. 729-736 (1973).

Muraoka, T. et al., "Muscle fiber and tendon length changes in the human vastus lateralis during show pedaling," J. Appl. Physiol., 91: 2035-2040 (2001).

Nakagawa, A., "Intelligent Knee Mechanism and the Possibility to Apply the Principle to the Other Joints," paper presented at the Proceedings of the $20^{th}$ Annual International Conference of the IEEE Engineering in Medicine and Biology Society, 20(5): 2282-2287 (1998).

Neal, R. M. et al., "A View of the EM Algorithm That Justifies Incremental, Sparse, and Other Variants," pp. 1-14.

Ng, S.K. et al., "Fuzzy Model Identification for Classification of Gait Events in Paraplegics," IEEE Transactions on Fuzzy Systems, 5(4) (1997).

Nielsen, D.H. et al., "Comparison of Energy Cost and Gait Efficiency during Ambulation in Below-Knee Ampuees Using Different Prosthetic Feet," *JPO*, 1:24-31, http://www.oandp.org/jpo/library/1989_01_024.asd, Retrieved on: Feb. 7, 2012.

Oda, T. et al. "In Vivo Length-Force Relationships on Muscle Fiber and Muscle Tendon Complex in the Tibialis Anterior Muscle," *International Journal of Sport and Health Sciences*, 3:245-252 (2005).

Ogihara, N., and Yamazaki, N., "Generation of Human Bipedal Locomotion by a Bio-Mimetic Neuro-Musculo-Skeletal Model," *Biol. Cybern.*, 84: 1-11 (2001).

Palmer, M.L., "Sagittal Plane Characterization of Normal Human Ankle Function Across a Range of Walking Gait Speeds," Unpublished master's thesis, Massachusetts Institute of Technology, Massachusetts (2002).

Paluska, D., and Herr, H., "Series Elasticity and Actuator Power Output," paper presented at the Proceedings of the 2006 IEEE International Conference on Robotics and Automation (2006).

Paluska, D., and Herr H., "The Effect of Series Elasticity on Actuator Power and Work Output: Implications for Robotic and Prosthetic Joint Design," Robotics and Autonomous Systems, 54:667-673 (2006).

Pang, M.Y.C. and Yang, J.F., "The Initiation of the Swing Phase in Human Infact Stepping: Importance of Hip Position and Leg Loading," Journal of Physiology, 528(2):389-404 (2000).

Dubowsky, S., "Transactions of the ASME," Journal of Mechanisms, Transmissions, and Automation in Design, 106(1): 102-107 (1984).

Paul, C., et al., "Development of a Human Neuro-Musculo-Skeletal Model for Investigation of Spinal Cord Injury," Biol. Cybern., 93:153-170 (2005).

Pearson, K., et al., "Assessing Sensory Function in Locomotor Systems Using neurp-mechanical Simulations," Trends in Neurosciences, 29(11): 626-631 (2006).

Pearson, K.G., "Generating the Walking Gait: Role of Sensory Feedback," Progress in Brain Research, 143:123-129 (2004).

Perry, J., et al., "Efficiency of Dynamic Elastic Response Prosthetic Feet," Journal of Rehabilitation Research, 30(1):137-143 (1993).

Davids, J.R., "Book Reviews" Journal of Pediatric Orthopedics, pp. 815, No date given.

Petrofsky, J.S.., et al., "Feedback Control System for Walking in Man," Comput. Biol. Med. 14(2):135-149 (1984).

Pfeffer, L.E., et al., "Experiments with a Dual-Armed, Cooperative, Flexible-Drivetrain Robot System," paper presented at the IEEE, Aerospace Robotics Laboratory, Department of Aeronautics and Astronautics, Stanford University (1993).

Popovic, M., et al., "Angular Momentum Primitives for Human Walking: Biomechanics and Control," paper presented at the Proceedings IEEE/RSJ International Conference on Intelligent Robots and Systems, 1685-1691 (2004).

Popovic, M., et al., "Angular Momentum Regulation During Human Walking: Biomechanics and Control," paper presented at the Proceedings IEEE International Conference on Robotics and Automation, 2405-2411 (2004).

Popovic, M., et al., "Conservation of Angular Momentum During Human Locomotion," MIT Artificial Intelligence Laboratory, pp. 231-232 (2002).

Popovic, D., et al., "Control Aspects of Active Above-Knee Prosthesis," Int. J. Man-Machine Studies, 35:751-767 (1991).

Popovic, D. and Sinkjacr, T., "Control of Movement for the Physically Disabled: Control for Rehabilitation Technology," (Springer Publisher) pp. 270-302, No date given.

Popovic, M.R., et al., "Gait Identification and Recognition Sensor," paper presented at the Proceedings of $6^{th}$ Vienna International Workshop on Functional Electrostiumlation (Sep. 1998).

Popovic, M.B. and Herr, H., "Global Motion Control and Support Base Planning," pp. 1-8.

Popovic, M.B. and Herr, H., "Ground Reference Points in Legged Locomotion: Definitions, Biological Trajectories and Control Implications," Mobile Robots Towards New Applications, ISBN 3-86611-314-5, pp. 79-104 (2006).

Popovic, M.B., et al., "Zero Spin Angular Momentum Control: Definition and Applicability," pp. 1-16.

Pratt, G.A., "Legged Robots at MIT: What's New Since Raibert." Paper presented at the meeting of the IEEE, Robotics and Automation Magazine (Sep. 2000).

Pratt, G.A., "Low Impedance Walking Robots," Integ. and Comp. Biol., 42: 174-181 (2002).

Pratt, J.E., et al., "The RoboKnee: An Exoskeleton for Enhancing Strength and Endurance During Walking." Paper presented at the Proceedings of the 2004 IEEE International Conference on Robotics & Automation, New Orleans, LA (Apr. 2004).

Pratt, G.A. and Williamson, M.M., "Series Elastic Actuators." Paper presented at the meeting of the IEEE, pp. 399-406 (1995).

Prochazka, A. and Yakovenko, S., "The Neuromechanical Tuning Hypothesis," Progress in Brain Research, 165: 257-267 (2007).

Prochazka, A., et al., "Sensory Control of Locomotion: Reflexes Versus Higher-Level Control," Sensorimotor Control of Movement and Posture, pp. 357-367 (2002).

Prochazka, A., et al., "Positive Force Feedback Control of Muscles," The American Physiological Society, pp. 3226-3236 (1997).

Raibert, M.H., "Legged Robots that Balance," MIT Press, Cambridge, MA, p. 89 (1985).

Rassier, D.E., et al., "Length Dependence of Active Force Production in Skeletal Muscle," The American Physiological Society, pp. 1445-1457 (1999).

Riener, R., et al., "Stair Ascent and Descent at Different Inclinations," Gait and Posture, 15: 32-44 (2002).

Rietman, J.S., et al., "Gait Analysis in Prosthetics: Opinions, Ideas and Conclusions," Prosthetics and Orthotics International, 26: 50-57 (2002).

Robinson, D.W., "Design and Analysis of Series Elasticity in Closed-Loop Actuator Force Control." Unpublished doctoral dissertation, Massachusetts Institute of Technology (2000).

Robinson, D.W., et al., "Series Elastic Actuator Development for a Biomimetic Walking Robot." Paper presented at the IEEE/ASME International Conf. on Adv. Intelligent Mechatronics (Sep. 19-22, 1999).

Rosen, J., et al., "A Myosignal-Based Powered Exoskeleton System," IEEE Transaction on Systems, Man, and Cybernetics—Part A: Systems and Humans, 31(3): 210-222 (2001).

Ruina, A., et al., "A Collisional Model of the Energetic Cost of Support Work Qualitatively Explains Leg Sequencing in Walking and Galloping, Pseudo-Elastic Leg Behavior in Running and the Walk-To-Run Transition," J. of Theoretical Biology, 237: 170-192 (2005).

Rybak, I.A., et al., "Modelling Spinal Circuitry Involved in Locomotor Pattern Generation: Insights from Deletions During Fictive Locomotion," J. Physiol., 577(2): 617-639 (2006).

Rybak, I.A., et al., "Modelling Spinal Circuitry Involved in Locomotor Pattern Generation: Insights from the Effects of Afferent Stimulation," J. Physiol., 577(2): 641-658 (2006).

Sanderson, D.J. and Martin. P.E., "Lower Extremity Kinematic and Kinetic Adaptations in Unilateral Below-Knee Amputees During Walking," Gait & Posture, 6(2): 126-136 (1997).

Sanger, T.D., "Human Arm Movements Described by a Low-Dimensional Superposition of Principal Components," The J. of Neuroscience, 20(3): 1066-1072 (2000).

Saranli, U., et al., "RHex: A Simple and Highly Mobile Hexapod Robot," The International Journal of Robotics Research, pp. 616-631 (2001).

Sarrigeorgidis, K. and Kyriakopoulos, K.J., "Motion Control of the N.T.U.A. Robotic Snake on a Planar Surface." Paper presented at the Proceedings of the 1998 IEEE International Conference on Robotics & Automation, Leuven, Belgium (May 1998).

Schaal, S. and Atkeson, C.G., "Constructive Incremental Learning from Only Local Information," Neural Computation, 10(8): 2047-2084 (1998).

Schaal, S., "Is Imitation Learning the Route to Humanoid Robots?", Trends in Cognitive Sciences, 3: 233-242 (1999).

Scott, S.H. and Winter, D.A., "Biomechanical Model of the Human Foot: Kinematics and Kinetics During the Stance Phase of Walking," J. Biomechanics, 26(9): 1091-1104 (1993).

Sentis, L. and Khatib, O., "Task-Oriented Control of Humanoid Robots Through Prioritization." Paper presented at the IEEE-RAS/RSJ International Conference on Humanoid Robots, pp. 1-16.

Seyfarth, A., et al., "A Movement Criterion for Running," J. of Biomechanics, 35: 649-655 (2002).

Seyfarth, A., et al., "Stable Operation of an Elastic Three-Segment Leg," Biol. Cybern., 84: 365-382 (2001).

Seyfarth, A., et al., "Swing-Leg Retraction: A Simple Control Model for Stable Running," The J. of Experimental Biology, 206: 2547-2555 (2003).

Giszter et al., "Convergent Force Fields Organized in the Frog's Spinal Cord," The Journal of Neuroscience, Feb. 1993, pp. 467-491.

Sinkjaer, T., et al., "Major role for sensory feedback in soleus EMG activity in the stance phase of walking in man," Journal of Physiology, 523.3: 817-827 (2000).

Skinner, H.B., and Effeney, D.J., "Gait Analysis in Amputees," American Journal of Physical Medicine, 64(2): 82-89 (1985).

Smidt, G.L., et al., "An Automated Accelerometry System for Gait Analysis," J. Biomechanics,10: 367-375 (1977).

Srinivasan, M., "Energetics of Legged Locomotion: Why is Total Metabolic Cost Proportional to the Cost of Stance Work." ISB XXth Congress—ASB 29th Annual Meeting, Cleveland, OH (Jul. 31-Aug. 5.

Stepien, J., et al.. "Activity Levels Among Lower-Limb Amputees: Self-Report Versus Step Activity Monitor," *Arch. Phys. Med. Rehabil.*, 88: 896-900 (2007).

Sugano, S., et al., "Force Control of the Robot Finger Joint equipped with Mechanical Compliance Adjuster," Proceedings of the 1992 IEEE/RSJ International Conference on Intelligent Robots and Systems, Raleigh, NC (Jul. 1992).

Sugihara, T., et al., "Realtime Humanoid Motion Generation through ZMP Manipulation based on Inverted Pendulum Control," Proceedings of the 2002 IEEE International Conference on Robotics & Automation, Washington, DC (May 2002).

Sup, F., et al., "Design and Control of a Powered Transfemoral Prosthesis," *The International Journal of Robotics Research*, 27(2): 263-273 (2008).

Taga, G., "A model of the neuro-musculo-skeletal system for human locomotion," *Biol. Cybern.*, 73: 97-111 (1995).

Takayuki, F., et al., "Biped Locomotion using Multiple Link Virtual Inverted Pendulum Model," *T.IEE Japan.* 120-C (2): 208-214 (2000).

Thoroughman, K., and Shadmehr, R., "Learning of action through adaptive combination of motor primitives," *Nature*, 407: 742-747(2000).

Tomović, R., and McHee, R.B., "A Finite State Approach to the Synthesis of Bioengineering Control Systems," *IEEE Transactions on Human Factors in Electronics*, 7(2): 65-69 (1966).

Tong, K., and Granat, M., "A practical gait analysis system using gyroscopes," *Medical Engineering & Physics*, 21: 87-94 (1999).

Türker, K., "Electromyography: Some Methodological Problems and Issues," *Phys. Ther.*, 73: 698-710 (1993).

Van den Bogert, A. J., et al., "A Method for Inverse Dynamic Analysis Using Accelerometry," *J. Biochemechanics*, 29(7): 949-954 (1996).

Van den Bogert, A. J., "Exotendons for Assistance of Human Locomotion," Biomedical Engineering OnLine, BioMed Central, 2(17):1-8 (2003).

Veltink, P.H., et al., "The Feasibility of Posture and Movement Detection by Accelerometry," paper presented at the IEEE meeting (1993).

Vukobratovic, M., Juricic, D., "Contribution to the Synthesis of Biped Gait," paper presented at the IEEE Transactions on Bio-Medical Engineering, BME-16(1) (Jan. 1969).

Vukobratovic, M., and Stepanenko, J., :Mathematical Models of General Anthropomorphic Systems, Mathematical Biosciences, 17: 191-242 (1973).

Walsh, C.J., et al., "Biomimetic Design of an Under-Actuated Leg Exoskeleton for Load-Carrying Augmentation," Unpublished Master's thesis, Massachusetts Institute of Technology, Cambridge, MA (2006).

Waters, R.L., et al., "Energy Cost of Walking of Amputees: The Influence of Level of Amputation," *The Journal of Bone and Joint Surgery*, 58A(1): 42-46 (1976).

Wilkenfeld, A., and Herr, H., "An Auto-Adaptive External Knee Prosthesis," MIT Lab., No date given.

Wilkenfeld, A., "Biologically Inspired Autoadaptive Control of a Knee Prosthesis," unpublished doctoral dissertation, Massachusetts Institute of Technology, Cambridge, MA (2000).

Willemsen, A.Th.M., et al., "Automatic Stance-Swing Phase Detection from Accelerometer Data for Peroneal Nerve Stimulation," presented at the meeting of IEEE Transactions on Biomedical Engineering, 37(12):1201-1208 (1990).

Willemsen, A.Th.M., et al., "Real-Time Gait Assessment Utilizing a New Way of Accelerometry," *J. Biomechanics*, 23(8):859-863 (1990).

Williams, B.C., et al., "Mode Estimation of Model-Based Programs: Monitoring Systems with Complex Behavior," paper submitted to Massachusetts Institute of Technology, Cambridge, MA, No date given.

Williamson, M.M., "Series Elastic Actuators," A.I. Technical Report submitted to Massachusetts Institute of Technology, Cambridge, Massachusetts (Jan. 1995).

Winter, D.A., and Sienko, S.E., "Biomechanics of Below-Knee Amputee Gait," *J. Biomechanics*, 21(5):361-367 (1988).

Winter, D.A., "Energy Generation and Absorption at the Ankle and Knee during Fast, Natural, and Slow Cadences," *Clinical Orthopedics and Related Research*, 175: 147-154 (1983).

Winter, D.A., and Robertson, D.G.E., "Joint Torque and Energy Patterns in Normal Gait," Biol. Cybernetics, 29:137-142 (1978).

Wisse, M., "Essentials of Dynamic Walking: Analysis and Design of Two-legged Robots," No date given.

Woodward, M.I. and Cunningham, J.L., "Skeletal Accelerations Measured During Different Exercises," *Proc. Instn. Mech. Engrs.*, 207: 79-85 (1993).

Wu, G. and Ladin, Z., "The Study of Kinematic Transients in Locomotion Using the Integrated Kinematic Sensor," *IEEE Transactions on Rehabilitation Engineering*, 4(3): 193-200 (1996).

Yakovenko, S., et al., "Contribution of Stretch Reflexes to Locomotor Control: A Modeling Study," *Biol. Cybern.*, 90: 146-155 (2004).

Yun, X., "Dynamic State Feedback Control of Constrained Robot Manipulators." Paper presented at the Proceedings of the 27th Conference on Decision and Control, Austin, TX (Dec. 1988).

Zlatnik, D., et al., "Finite-State Control of a Trans-Femoral (TF) Prosthesis," *IEEE Transactions on Control Systems Technology*, 10(3): 408-420 (2002).

\* cited by examiner

POWERED ARTIFICIAL KNEE WITH AGONIST-ANTAGONIST ACTUATION

RELATED APPLICATIONS

This application claims the benefit of U.S. Provisional Application Ser. No. 61/148,545, filed Jan. 30, 2009, the entire disclosure of which is herein incorporated by reference in its entirety.

This application is a continuation-in-part of co-pending U.S. patent application Ser. No. 12/608,627, filed Oct. 29, 2009, which is a continuation of U.S. patent application Ser. No. 11/642,993, filed Dec. 19, 2006, now abandoned, which claims the benefit of U.S. Prov. Pat. App. Ser. No. 60/751,680, filed on Dec. 19, 2005, and is a continuation-in-part of U.S. patent application Ser. Nos. 11/395,448, 11/495,140, and 11/600,291, listed below, and 11/499,853, now U.S. Pat. No. 7,313,463, which claims the benefit of the filing date of U.S. Prov. Pat. App. Ser. No. 60/705,651, filed on Aug. 4, 2005, and is a continuation-in-part of U.S. patent application Ser. No. 11/395,448, listed below, the entire disclosures of which are incorporated by reference herein in their entirety.

This application is also a continuation-in-part of U.S. patent application Ser. No. 11/395,448, entitled "Artificial human limbs and joints employing actuators, springs, and Variable-Damper Elements", filed on Mar. 31, 2006 by Hugh M. Herr, Daniel Joseph Paluska, and Peter Dilworth. U.S. patent application Ser. No. 11/395,448 claims the benefit of the filing date of U.S. Prov. Pat. App. Ser. No. 60/666,876, filed on Mar. 31, 2005, and the benefit of the filing date of U.S. Prov. Pat. App. Ser. No. 60/704,517, filed on Aug. 1, 2005.

This application is also a continuation-in-part of U.S. patent application Ser. No. 11/495,140, entitled "An Artificial Ankle-Foot System with Spring, Variable-Damping, and Series-Elastic Actuator Components", filed on Jul. 29, 2006 by Hugh M. Herr, Samuel K. Au, Peter Dilworth, and Daniel Joseph Paluska. U.S. patent application Ser. No. 11/495,140 claims the benefit of the filing date of U.S. Prov. Pat. App. Ser. No. 60/704,517, filed on Aug. 1, 2005, and was also a continuation-in-part of U.S. patent application Ser. No. 11/395,448.

This application is also a continuation-in-part of U.S. patent application Ser. No. 11/600,291, entitled "Exoskeletons for running and walking", filed on Nov. 15, 2006 by Hugh M. Herr, Conor Walsh, Daniel Joseph Paluska, Andrew Valiente, Kenneth Pasch, and William Grand. U.S. patent application Ser. No. 11/600,291 claims the benefit of the filing date of U.S. Prov. Pat. App. Ser. No. 60/736,929, filed on Nov. 15, 2005, and is a continuation-in-part of U.S. patent application Ser. Nos. 11/395,448, 11/499,853, and 11/495,140.

The present application claims the benefit of the filing date of each of the foregoing patent applications and incorporates the disclosure of each of the foregoing applications herein by reference.

STATEMENT REGARDING FEDERALLY SPONSORED RESEARCH OR DEVELOPMENT

This invention was made with U.S. government support under Grant Numbers VA241-P-0026; 650D70025 and VA241-P-0479, 650-D85022, awarded by the United States Veterans Administration. The government has certain rights in this invention.

FIELD OF THE TECHNOLOGY

The present invention relates to artificial joints and limbs for use in prosthetic, exoskeletal, orthotic or robotic devices and, in particular, to powered artificial knee joints.

BACKGROUND

Most commercial lower-extremity prostheses and orthoses are passive and cannot provide positive mechanical power to replicate joint biomechanics during the gait cycle. Existing approaches to the design of powered knee systems have focused mainly on the use of single motor-transmission systems directly coupled to the joint. Such direct-drive designs, however, require high electrical power consumption in order to fully emulate the mechanical behavior of the biological knee joint even during level-ground ambulation. One reason for this lack of energetic economy is inadequate use of the passive dynamics of the leg, and elastic energy storage and return of tendon-like structures.

Knee prostheses for above-knee amputees can be classified into three major groups: passive, variable-damping, and powered. Passive prosthetic knees do not require a power supply for their operation, and are generally less adaptive to environmental disturbances than variable-damping prostheses. Variable-damping knees do require a power source, but only to modulate damping levels, whereas powered prosthetic knees are capable of performing non-conservative positive knee work.

Variable-damping knees offer several advantages over mechanically passive designs, including enhanced knee stability and adaptation to different ambulatory speeds. Although variable-damping knees offer some advantages over purely passive knee mechanisms, they are nonetheless incapable of producing positive mechanical power and therefore cannot replicate the positive work phases of the human knee joint for such activities as sit-to-stand maneuvers, level-ground walking, and stair/slope ascent ambulation. Not surprisingly, transfemoral amputees experience clinical problems when using variable-damping knee technology, such as, for example, asymmetric gait patterns, slower gait speeds, and elevated metabolic energy requirements compared to non-amputees.

SUMMARY

Current approaches to the design of powered prostheses, orthoses, exoskeletons, and robotic legged systems have focused mainly on the use of single motor-transmission systems directly coupled to the joints. Such direct-drive designs require high electrical power consumption to fully emulate the mechanical behavior of the human leg. The biomimetic knee presented here leverages passive dynamics, and uses elastic energy storage and return of tendon-like structures, to minimize the electrical power requirements. The knee is capable of replicating human-like knee mechanics during level ground walking at low electrical power consumption from an onboard power supply.

In one aspect, the invention is a knee prosthesis that comprises an agonist-antagonist arrangement of two series-elastic actuators positioned in parallel. The prosthetic knee design is motivated by a variable-impedance prosthetic knee model, comprising two series-elastic clutch mechanisms and a variable-damper. Human gait data are utilized to constrain the model's joint to move biologically. Model parameters are then obtained using an optimization scheme that minimizes the sum over time of the squared difference between the model's knee joint torque and biological knee values. The optimized values are then used to specify the mechanical and finite state control design of the agonist-antagonist knee prosthesis. Two preferred embodiments have been developed.

Because of its architecture, the knee according to the invention can be controlled to behave as agonist-antagonist, series-elastic clutch elements during the stance phase of the gait cycle, and as a variable-damper during the swing phase, resulting in an energetically-economical artificial knee device for level-ground walking. The knee embodiments are fully motorized with series-elastic force sensing, thus, knee joint torque can be directly controlled for more energetically expensive tasks, such as stair and ramp ascent gaits, as well as standing from a seated posture. Hence, the knee architecture is designed to accommodate non-conservative, high mechanical power movements, while still providing for a highly economical level-ground walking mode.

In one aspect, the invention disclosed is a powered knee prosthesis comprising a knee joint that is rotatable and coupleable to an artificial leg member, a series-elastic flexion actuator connected to the knee joint in parallel with the leg member, for applying a force to cause rotation of the knee joint, resulting in flexion of the leg member, a series-elastic extension actuator, connected to the knee joint in parallel with the leg member on the opposite side of the leg member from the flexion actuator, for applying a force to cause rotation of the knee joint, resulting in extension of the leg member, and a controller for independently energizing the flexion motor and the extension motor at different times to control the movement of the knee joint and coupled leg member. The flexion actuator comprises the series combination of a flexion motor and a flexion elastic element and the extension actuator comprises the series combination of an extension motor and an extension elastic element. In a preferred embodiment, at least one sensor is employed to provide feedback to the controller. Sensors preferably include, but are not limited to, those responsive to angular displacement and acceleration of the knee joint, torque at the knee joint, compression of the flexion elastic element, compression of the extension elastic element, rotation of the flexion motor, rotation of the extension motor, and/or contact with the walking surface.

In one preferred embodiment, the flexion actuator and the extension actuator are unidirectional, and the flexion elastic element and the extension elastic element are series springs. In another preferred embodiment, the flexion actuator is unidirectional, the extension actuator is bidirectional, the flexion elastic element is a series spring, and the extension elastic element is a set of pre-compressed series springs. In another preferred embodiment, particularly adapted for variable-speed walking, the flexion elastic element is a non-linear softening spring and the extension elastic element is a non-linear hardening spring.

BRIEF DESCRIPTION OF THE DRAWINGS

Other aspects, advantages and novel features of the invention will become more apparent from the following detailed description of the invention when considered in conjunction with the accompanying drawings wherein.

DETAILED DESCRIPTION

A variable-impedance knee prosthesis according to the invention has two series-elastic actuators arranged in parallel in an agonist-antagonist arrangement. The prosthetic knee model comprises a variable damper and two series-elastic clutch units spanning the knee joint. A variable-impedance control design produces human-like knee mechanics during steady-state level-ground walking. Because of the variable-impedance nature of the prosthesis, electrical power requirements are modest while walking, allowing for an energetically-economical powered knee. In one application, a variable-impedance knee prosthesis according to the invention is advantageously employed as a part of a non-tethered biomimetic robotic leg.

As used herein, the following terms expressly include, but are not to be limited to:

"Actuator" means a type of motor, as defined below.

"Agonist" means a contracting element that is resisted or counteracted by another element, the antagonist.

"Agonist-antagonist actuator" means a mechanism comprising (at least) two actuators that operate in opposition to one another: an agonist actuator that, when energized, draws two elements together and an antagonist actuator that, when energized, urges the two elements apart.

"Antagonist" means an expanding element that is resisted or counteracted by another element, the agonist.

"Biomimetic" means a human-made structure or mechanism that mimics the properties and behavior of biological structures or mechanisms, such as joints or limbs.

"Dorsiflexion" means bending the ankle joint so that the end of the foot moves upward.

"Elastic" means capable of resuming an original shape after deformation by stretching or compression.

"Extension" means a bending movement around a joint in a limb that increases the angle between the bones of the limb at the joint.

"Flexion" means a bending movement around a joint in a limb that decreases the angle between the bones of the limb at the joint.

"Motor" means an active element that produces or imparts motion by converting supplied energy into mechanical energy, including electric, pneumatic, or hydraulic motors and actuators.

"Plantarflexion" means bending the ankle joint so that the end of the foot moves downward.

"Spring" means an elastic device, such as a metal coil or leaf structure, which regains its original shape after being compressed or extended.

Figure 1A:
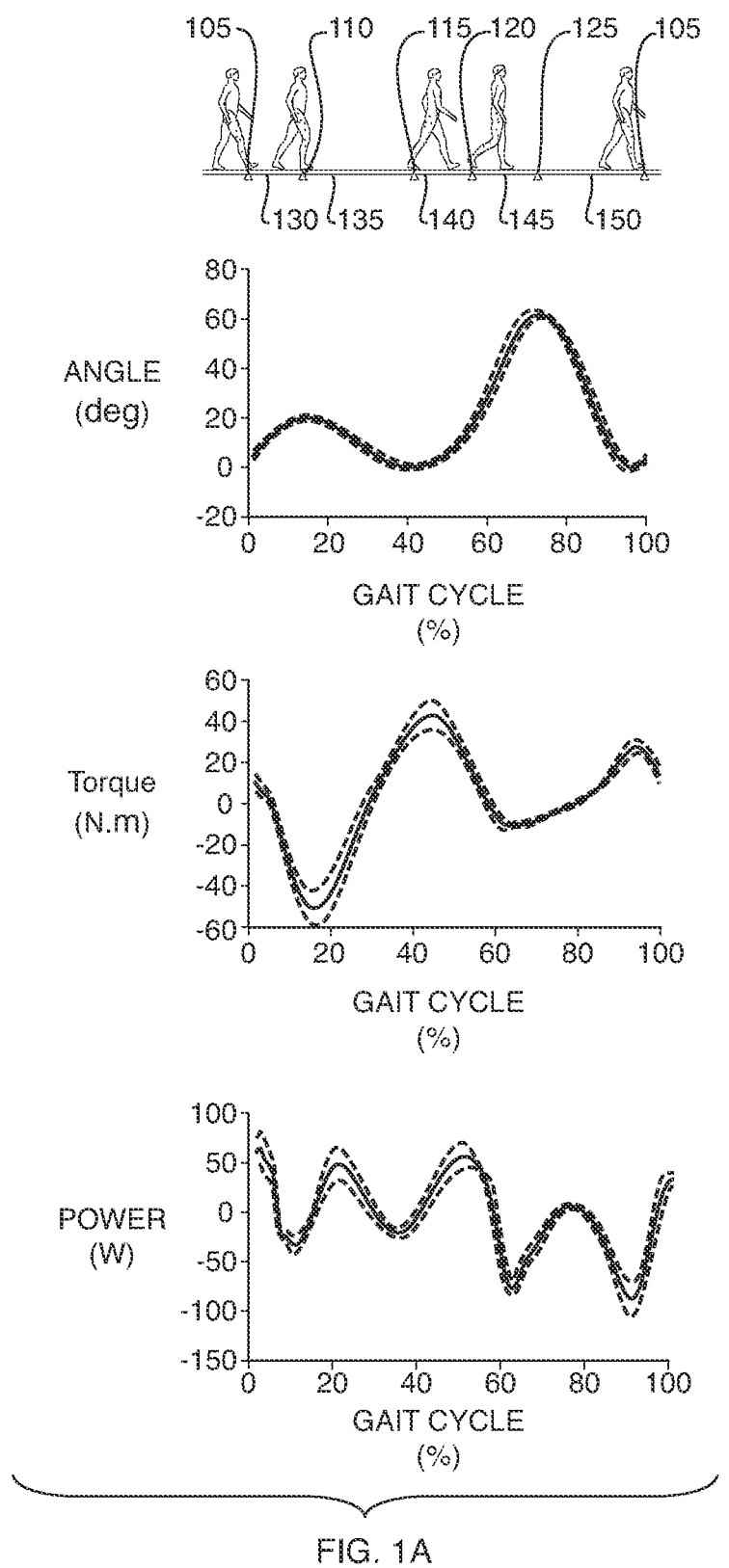
FIGS. 1A and 1B graphically depict representative knee biomechanics in level-ground walking, with FIG. 1A being the knee angle, torque, and power curves of a study participant with intact knee joints plotted against percent gait cycle during level ground walking at a self selected speed and FIG. 1B being a plot of knee torque vs. knee angular position, showing the five phases of gait.
Figure 1B:
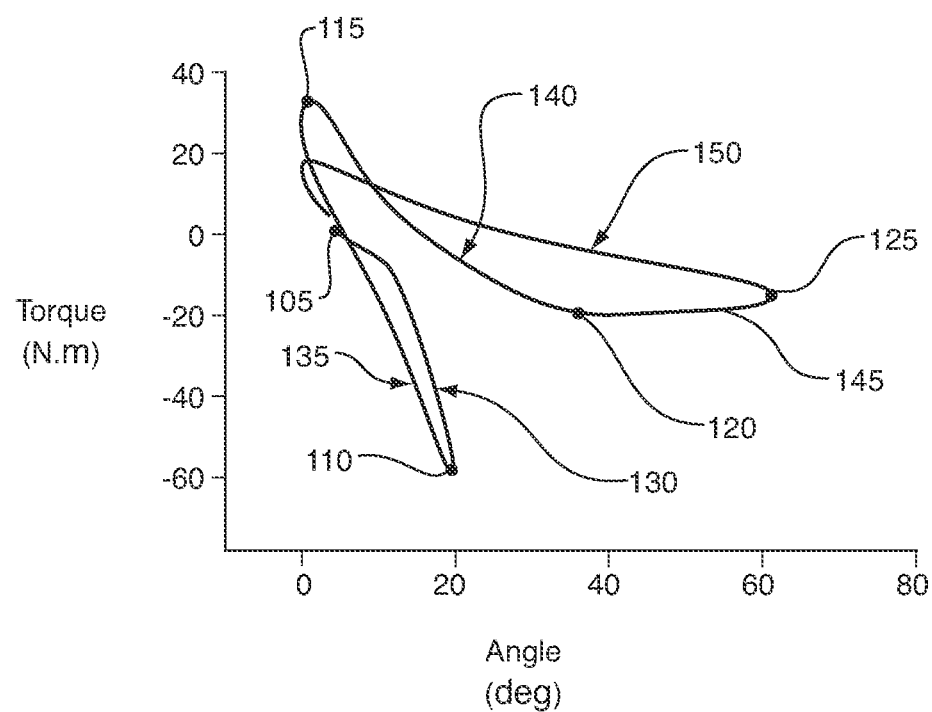

Human Knee Biomechanics in Level Ground Walking FIGS. 1A and 1B graphically depict representative human knee biomechanics in level-ground walking In FIG. 1A, the knee angle, torque, and power curves of a male study participant (Mass=81.9 kg) are plotted against percent gait cycle during level ground walking at a self selected speed (1.31 m/sec). Plotted are mean (solid line; N=10 gait trials) about one standard deviation (dashed lines). In FIG. 1B, knee torque is plotted vs. knee angular position showing the five phases of gait. Key gait events separating the five phases are: heel strike (HS) 105, maximum stance flexion (MSF) 110, maximum stance extension (MSE) 115, toe off (TO) 120, and maximum swing flexion (MWF) 125.

As seen in FIGS. 1A and 1B, five distinct stages or gait phases have been used to describe knee biomechanics in level-ground walking. These gait phases are described as follows:

(1) Beginning at heel strike (HS) 105, the stance knee begins to flex slightly (~15 degrees). This Stance Flexion 130 phase allows for shock absorption upon impact. During this phase, the knee can be modeled as a spring (linear torque vs. angle slope; see FIG. 1B), storing energy in preparation for the Stance Extension phase 135.

(2) After maximum stance flexion (MSF) 110 is reached, the knee joint begins to extend (15% gait cycle), until maximum stance extension (MSE) 115 is reached (42% gait cycle). This knee extension period is called the Stance Extension phase 135. During Stance Extension 135, the knee acts as a spring (linear torque vs. angle slope; see FIG. 1B), having a similar stiffness to that of Stance Flexion 130. Here, stiffness is not actual joint stiffness but rather a quasi-static stiffness defined as the slope of the torque vs. angle curve.

(3) During late stance or Pre-Swing 140 (from 42% to 62% gait cycle), the knee of the supporting leg begins its rapid flexion period in preparation for Swing Flexion phase 145. During Pre-Swing 140, as the knee begins to flex in preparation for Toe-off 120, the knee acts as a spring (linear torque vs. angle slope; see FIG. 1B), but having a relatively lower stiffness than that during Stance Flexion 130 and Extension 135.

(4) As the hip is flexed, the leg leaves the ground and the knee continues to flex. At Toe-off 120, the Swing Flexion phase 145 of gait begins. Throughout this period (from 62% to 73% gait cycle), knee power is generally negative as the knee's torque impedes knee rotational velocity (see FIG. 1A). Thus, during Swing Flexion 145, the knee can be modeled as a variable damper.

(5) After reaching a maximum flexion angle (~60 degrees) during Swing Flexion 145, the knee begins to extend forward. During Swing Extension 150 (from 73% to 100% gait cycle), knee power is generally negative to decelerate the swinging leg in preparation for the next stance period. Thus, as with Swing Flexion 145, the knee during Swing Extension 150 can be modeled as a variable damper. After the knee has reached full extension, the foot, once again, is placed on the ground, and the next walking cycle begins.

Quasi-passive Prosthetic Knee Model and Optimization. Given the knee biomechanics described, there is a clear need for a variable-impedance knee prosthesis, capable of varying both damping and stiffness, that can produce human-like knee mechanics during steady-state level-ground walking. An example of such a prosthesis is the exemplary knee model, shown in FIG. 2A, comprising two antagonistic mono-articular series-elastic clutches 205, 210 (to model the stance phase knee mechanics) and one variable-damping element 215 (to model the swing phase mechanics). In the model, series springs 220, 225 can each be engaged by activating its respective clutch 205, 225, or disengaged by opening that clutch. As model constraints, each clutch can only be engaged once during each gait cycle. Additionally, once a clutch has been engaged, it only can be disengaged when the series spring has released all its energy and the force on the clutch is zero.

The series-elastic clutch model parameters were varied in order to match biomechanic behavior of the knee joint. The model parameters are two spring constants ($k_E$, $k_F$) corresponding to the extension and flexion spring stiffness, and the relative knee extension and flexion angles ($\theta_E$ and $\theta_F$), at which the extension and flexion springs become engaged during stance. By convention, the extensor spring tends to extend the knee joint when engaged, whereas the flexor spring tends to cause the knee to flex. The knee model was fitted to biomechanical data using an optimization scheme that minimized the sum over time of the squared difference between the model's knee joint torque and biological knee values. More specifically, the cost function used for the optimization was $$E_{cost}(k_F, k_E, \theta_E, \theta_F) = \sum_{i=1}^{100} \left( \frac{\tau^i_{bio} - \tau^i_{sim}}{\tau^{max}_{bio}} \right)^2 \quad (1)$$

where $\tau^i_{bio}$ and $\tau^i_{sim}$ are the angular torques applied about the knee joint at the ith percentage of gait cycle from the biological torque data and the knee model, respectively, and $\tau^{max}_{bio}$ is the maximum biological torque at the joint during the gait cycle. Cost function (1) was minimized with the constraint that the extensor spring always engages at heel strike ($\theta_E$=0). This constraint was applied to limit knee buckling at heel strike as a safety measure for the amputee.

The determination of the desired global minimum for cost function (1) was implemented by first using a genetic algorithm to find the region containing the global minimum, followed by an unconstrained gradient optimizer to determine the exact value of that global minimum. After optimizing cost function (1) by varying the parameters of the series-elastic clutch elements, the model's variable damper was used to achieve perfect agreement between the prosthetic knee model and biological torque values in regions where the series-elastic components were not able to absorb sufficient negative mechanical power. The biological knee torque values were obtained from an inverse dynamics calculation using kinetic and kinematic data from ten walking trials of a healthy 81.9 kg, 1.87 m tall subject walking at 1.31 m/s.

Figure 2A:
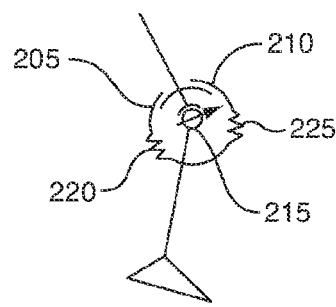
FIG. 2A is an exemplary embodiment of a variable-impedance prosthetic knee model, according to one aspect of the invention.
Figure 2B:
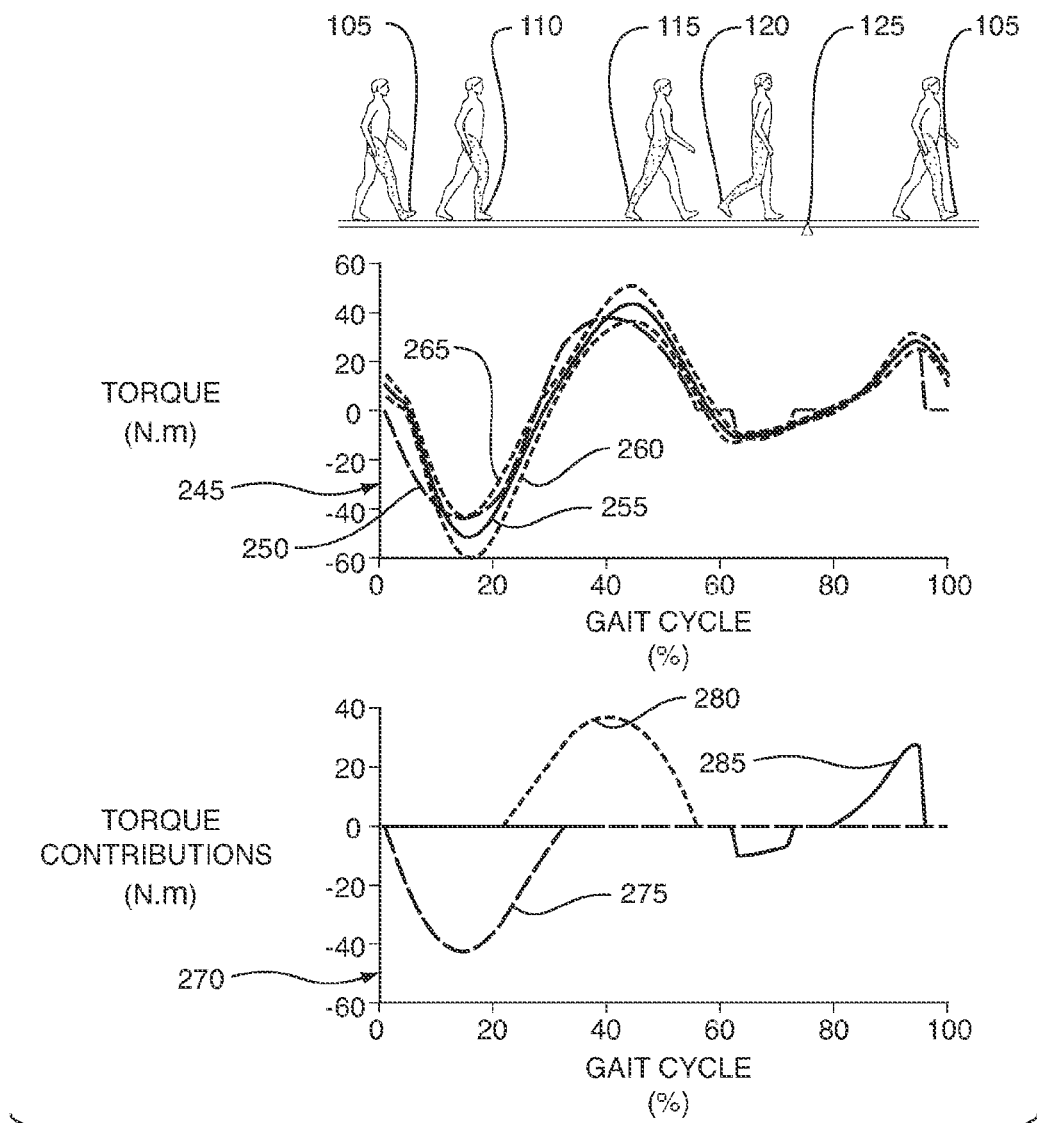
FIG. 2B depicts optimization results from the model of FIG. 2A, plotted against the biological torque data from FIGS. 1A-B.

FIG. 2B shows optimization results from the model of FIG. 2A, plotted against the biological torque data from FIGS. 1A-B. As shown in FIG. 2B, upper plot 245, optimized net torque output 250 of the knee model is compared to the torque profile of an intact human knee joint, with both mean 255 and one standard deviation 260, 265 shown (N=10 gait trials). Biological data, adopted from FIGS. 1A-B, are from a study participant (mass=81.9 kg) with intact limbs walking at a self-selected speed (walking speed=1.31 m/sec). Shown in lower plot 270 are the torque contributions from the extension 275 and flexion 280 springs of the series-elastic clutch elements, as well as from the variable damper 285. The optimizer gave an extension spring stiffness equal to $k_E$=160 N·m/rad, a flexion spring stiffness equal to 137 N·m/rad, and a knee engagement angle for the flexion spring equal to 0.27 radians (15.46 degrees).

The model's torque output agrees well with experimental values. As constrained by the optimization procedure, the extension spring engages at heel strike, storing energy during early stance knee flexion. As the knee begins to extend, the flexion spring is engaged, storing energy as the extension spring releases its energy. During the swing phase, the model's variable damper exactly matches the biological torque values in regions of negative power. At mid and terminal swing phase, the power is positive in the biological data, and thus, the damper outputs zero torque in these gait regions.

Figure 3:
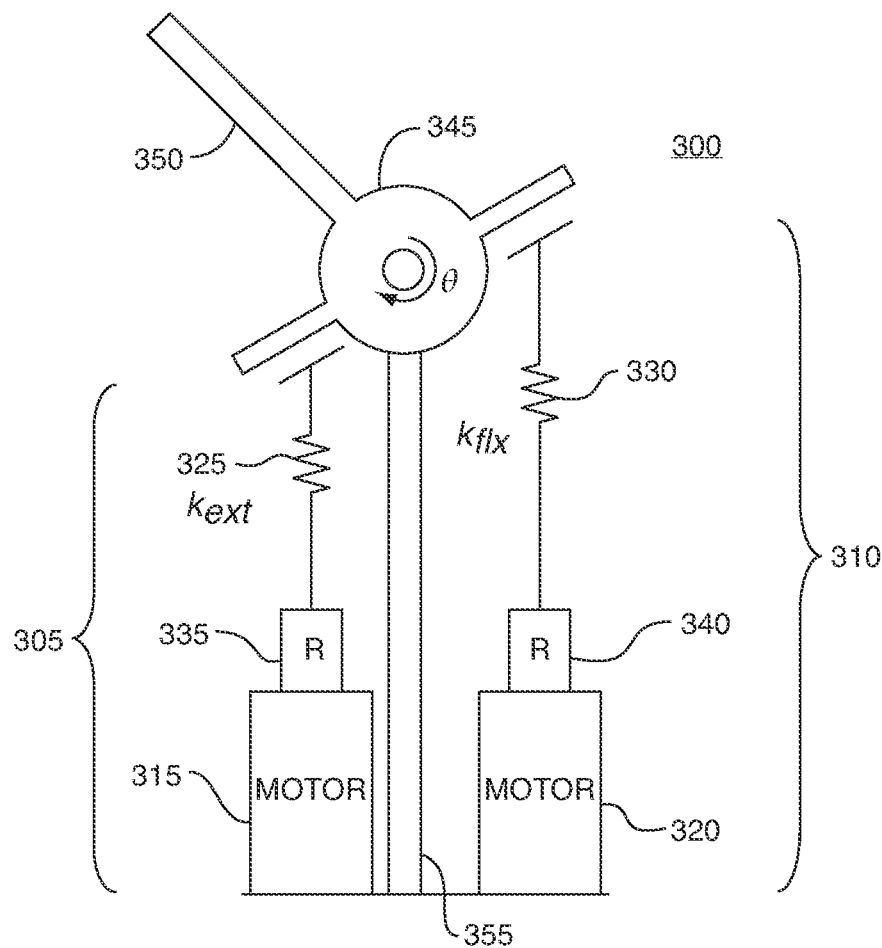
FIG. 3 is a simplified mechanical schematic of a powered agonist-antagonist knee, according to one aspect of the present invention.

A simplified mechanical schematic of an agonist-antagonist knee according to one aspect of the present invention is shown in FIG. 3. As depicted in FIG. 3, agonist-antagonist active knee prosthesis 300 comprises two unidirectional, series-elastic actuators, series-elastic extension actuator 305 and series-elastic flexion actuator 310. Each unidirectional actuator 305, 310 of knee prosthesis 300 consists of a motor 315, 320 and a series spring 325, 330, connected via a transmission 335, 340. The extension and flexion motors 315, 320 can be used independently to control the knee angle at which each series spring 325, 330 is engaged. Knee joint 345 between upper leg 350 and lower leg 355 is coupled to a linear carriage, that is free to move along the length of the device, by a cable drive transmission. This carriage can be engaged on either side by the extension and flexion springs 325, 330, each of which are positioned by a ball screw driven by an electric motor. In a preferred embodiment, both unidirectional, series-elastic actuators 305, 310 feature transmissions 335, 340 comprised of a 2:1 belt drive coupled to a ball screw (Nook industries, 10×3 mm).

Figure 4A:
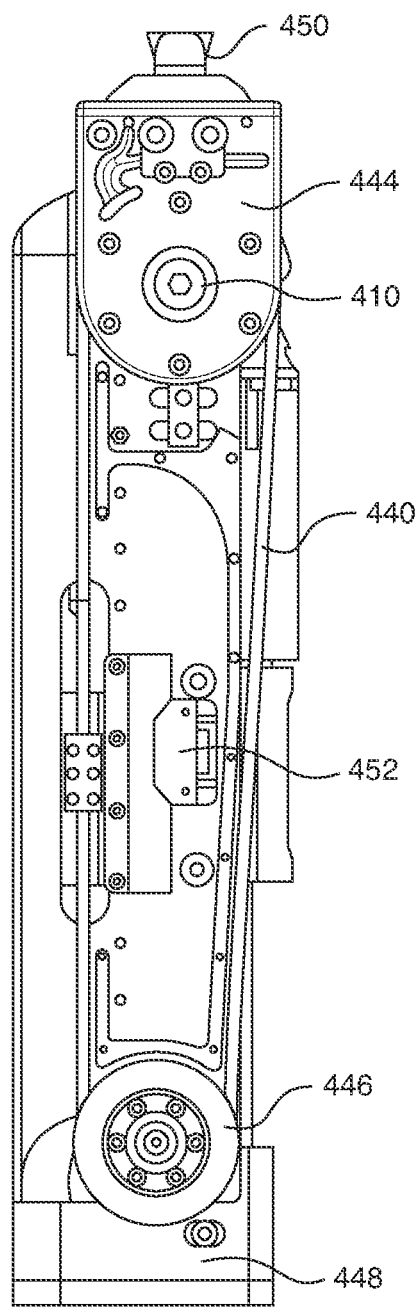
FIGS. 4A-C are lateral view, sagittal plane cut view, and posterior view schematics, respectively, of the mechanical design of an exemplary embodiment of an active knee prosthesis, according to the present invention.
Figure 4B:
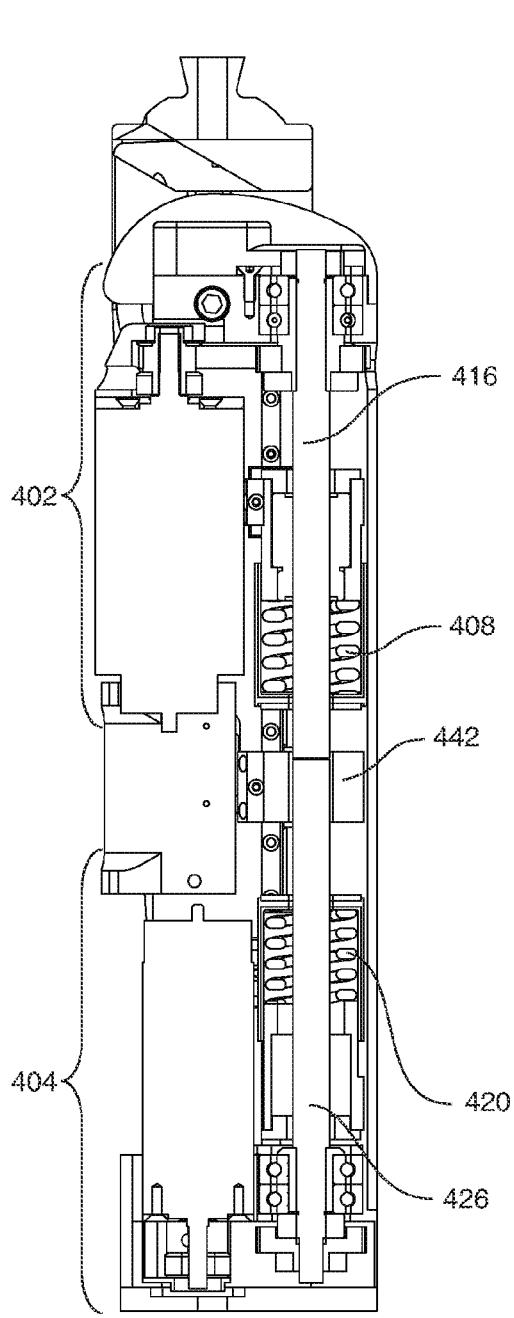
Figure 4C:
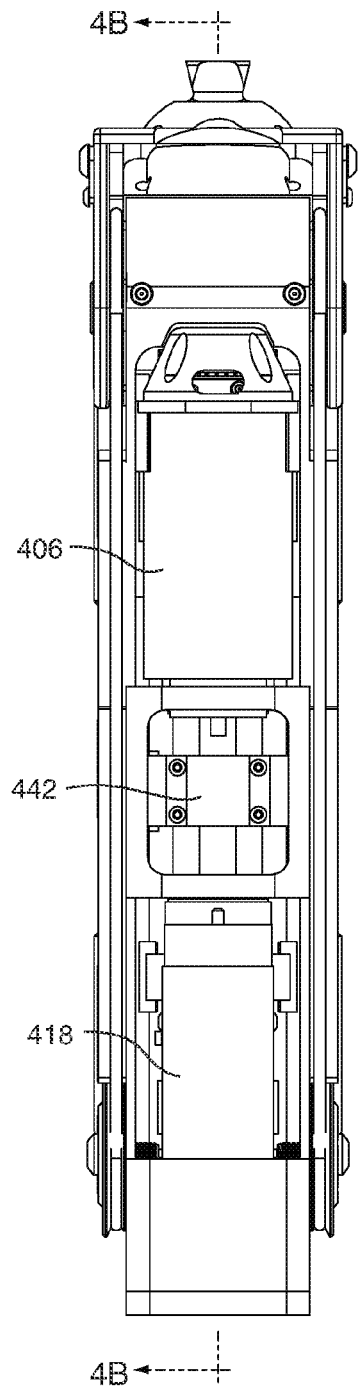
Figure 5:
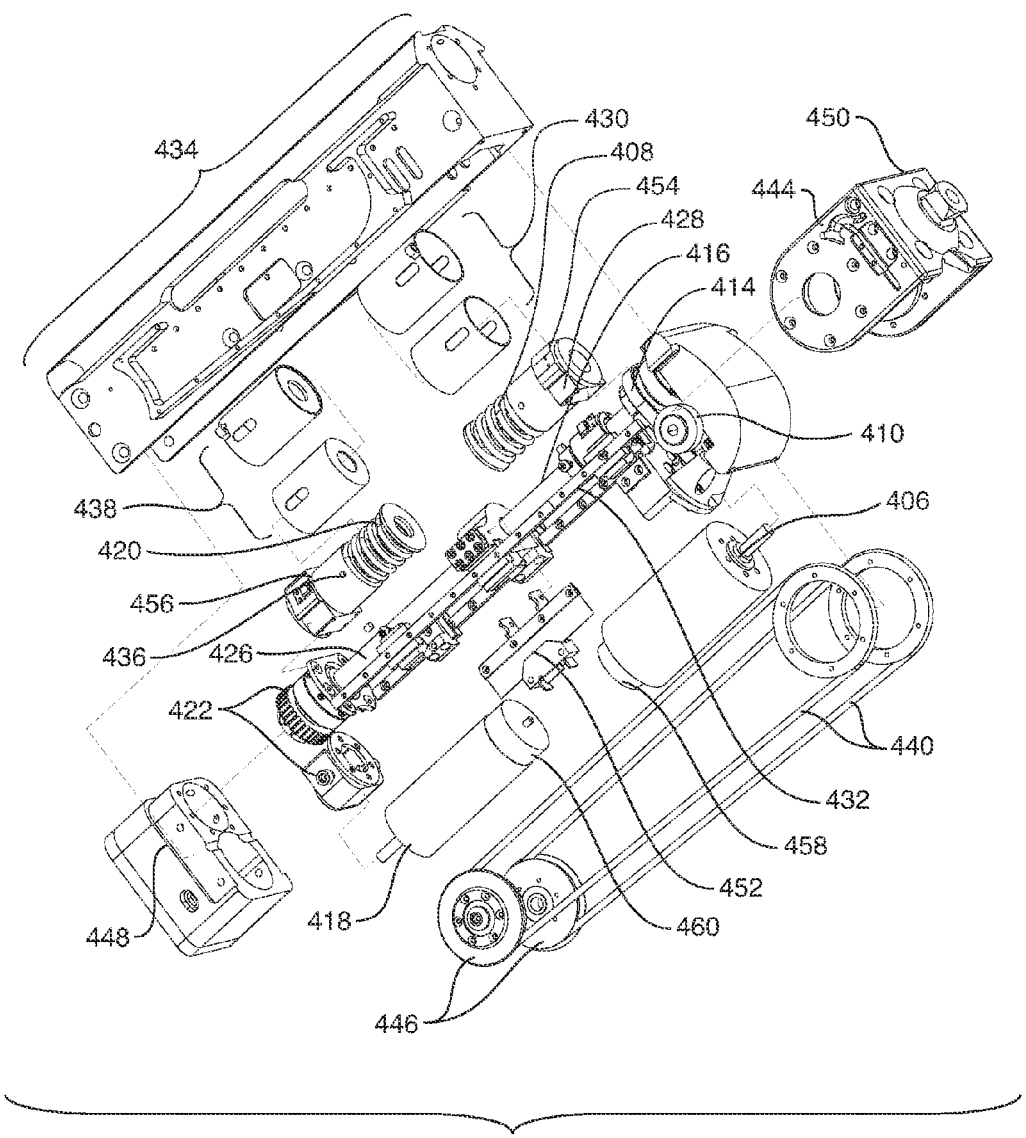
FIG. 5 is an exploded view of the main components of an exemplary embodiment of the active knee prosthesis of FIGS. 4A-C.
Figure 6:
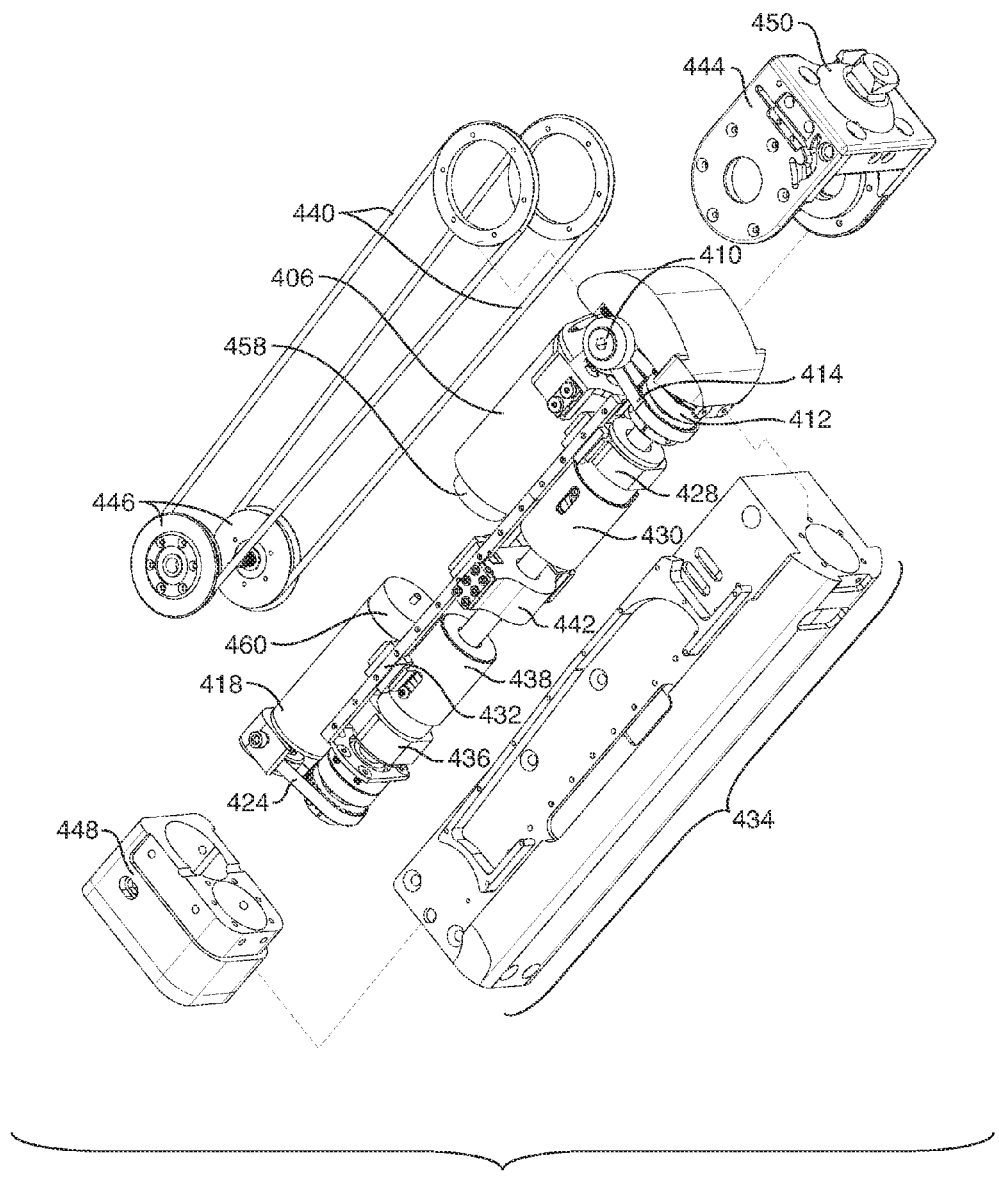
FIG. 6 is another exploded view of the main components of an exemplary embodiment of the active knee prosthesis of FIGS. 4A-C.

The principles of the exemplary knee model of FIG. 2A have been embodied in two exemplary preferred physical embodiments. In one preferred embodiment, shown in FIGS. 4A-C, an agonist-antagonist active knee prosthesis comprises two unidirectional, series-elastic actuators. FIGS. 5 and 6 are exploded views of the main components of the exemplary embodiment of an active knee prosthesis of FIGS. 4A-C.

As depicted in FIGS. 4A-C, 5, and 6, the unidirectional actuators are extension actuator 402 and flexion actuator 404. Extension actuator 402 of the knee prosthesis consists of extension motor 406 and series spring 408, connected via a transmission. The extension actuator is proximal to knee joint 410. The extension transmission consists of timing pulley 412 and belt 414 drive system coupled to precision ball-screw 416 drive. Flexion actuator 404 of the knee prosthesis consists of flexion motor 418 and series spring 420, connected via a transmission. The flexion transmission consists of a timing pulley 422 and belt 424 drive system coupled to precision ball-screw 426 drive. Extension actuator 402 and flexion actuator 404 can be used independently to control the knee joint 410 angle at which each series spring 408, 420 is engaged.

Series-elastic extension actuator 402 motorized element (extension electric motor 406) can be a brushed DC motor (such as Maxon's RE40 motor) or brushless DC motor (such as Maxon's EC-powermax 30). The extension motor directly drives a timing pulley-belt drive 412, 414 mechanism. This mechanism has a 1:2 transmission ratio. Timing pulley-belt drive mechanism 412, 414 actuates the rotation of ball-screw 416 (such as Nook industries, 10×3 mm). When ball-screw 416 of extension actuator 402 rotates, there is a linear displacement of coupled ball-nut housing 428. Ball-nut housing 428 is directly attached to extension series spring cage 430. Extension series spring cage 430 securely contains extension spring 408. Thus, when there is a linear displacement of coupled ball-nut housing 428, the extension series spring cage can have a linear displacement. The ball-nut housing moves along two linear precision steel guide rails 432 with minimal friction due to the linear bearings incorporated in the ball-nut housing. Each of the two precision guide rails 432 is attached to a corresponding inner lateral wall of main knee frame 434.

Series-elastic flexion actuator 404 motorized element (flexion electric motor 418) can be a brushed DC motor (such as Maxon's RE40, RE30 motors) or brushless DC motor (such as Maxon's EC-powermax 30 or 22). The extension motor directly drives a timing pulley-belt drive 422, 424 mechanism. This mechanism has a 1:2 transmission ratio. Pulley-belt drive mechanism 422, 424 actuates the rotation of ball-screw 426 (such as Nook industries, 10×3 mm). When ball-screw 426 of flexion actuator 404 rotates, there is a linear displacement of coupled ball-nut housing 436. Ball-nut housing 436 is directly attached to flexion series spring cage 438. Flexion series spring cage 438 securely contains flexion spring 420. Thus, when there is a linear displacement of coupled ball-nut housing 436, the flexion series spring cage can have a linear displacement. Ball-nut support 436 moves along two linear precision steel guide rails 432 with minimal friction due to the linear bearings incorporated in the ball-nut housing. Each of the two precision guide rails 432 is attached to a corresponding inner lateral wall of the main knee frame 434.

Knee joint 410 rotation is coupled to the linear displacement of linear carriage 442 attached to a cable drive transmission. The cable drive transmission is comprised of two steel cables 440. The two ends of each of steel cables 440 are attached to knee joint clevis support 444. Each cable loops around its corresponding joint pulley 446 located on each side of the knee. Each lateral joint pulley 446 has its axis attached to lower adaptor 448. Linear carriage 442 is supported and guided on two steel precision rail guides 432. Each rail runs along an inner lateral wall of main knee frame 434. Low friction between the precision rails and linear carriage 442 is obtained by the linear bearings incorporated inside linear carriage 442. Steel cables 440 allow the coupling of linear displacement from linear carriage 442 to the rotary motion of knee joint 410.

Linear carriage 442 can be independently be engaged by extension spring 408 and flexion spring 420 by means of their linear motion. Both springs are independently positioned by driving action of their corresponding series-elastic actuator. Each of series-elastic actuators 402, 404 are capable of providing sufficient power for both level-ground walking and more energetically expensive tasks such as stair ascent.

All actuation mechanisms are fully supported by an aluminum structure that corresponds to knee main frame 434, which has a design that resembles the lower limb anatomical envelope. The knee main frame has lower adaptor 448 that allows conventional and advanced robotic foot-ankle prosthesis to be attached to it. The coupling of knee joint clevis support 444 and the knee main frame produces the rotational degree of freedom that corresponds to knee joint 410. Knee joint clevis support 444 allows the mounting of a standard prosthetic pyramid adaptor 450, so that the knee prosthesis can be attached to a regular transfemoral socket and be worn by an amputee.

Based on such functional requirements, the design parameters for knee size, angular range, and maximum torque values for the embodiment of FIGS. 4A-C, 5, and 6 are listed in Table 1.

TABLE 1

| Height | 33 cm |
|---|---|
| Medio-Lateral Width | 7 cm |
| Anterior-Posterior Width | 7 cm |
| Total Weight | 3 Kg |
| Flexion Angle range | 0-120 deg |
| Max Output torque | 130 Nm |

Real-time feedback information to the on-board controller is provided by onboard intrinsic sensors. The sensors utilized by the embodiment of FIGS. 4A-C, 5, and 6 are listed in Table 2.

TABLE 2

| Measurement | Sensor |
|---|---|
| Knee angle | Digital encoder |
| Motor displacement | Digital encoder |
| Spring compression | Hall effect |
| Heel/Toe contact | Force sensitive resistor foot pad |

The angular displacement of the knee is measured indirectly with digital linear encoder 452 that is fixed on the external left side of knee main frame 434. The rotary motion of knee joint 410 is coupled to the displacement of linear carriage 442 via steel cable 440 transmission. The compression of each of the series elastic actuator's springs 408, 420 is measured with a corresponding hall-effect sensor 454, 456. These sensors measure the magnetic field change that occurs when there is a change to the proximity of a magnet that is attached to each of spring cages 430, 438 while springs 408, 420 are being compressed. The rotation of each motor is measured by motor digital encoder 458, 460 attached to the back of corresponding motor 406, 418. The interaction with the ground is measured with a force sensitive footpad (not pictured). This footpad allows detection of when the leg is on or off the walking surface and it assists the controller in determining what gait phase the user wearing the robotic knee prosthesis is in.

All electronics are implemented on a single on-board micro-controller based system. Motors are driven by H-bridge controllers with speed governed by 20 kHz pulse width modulation (PWM) and powered by DC battery (such as a six cell Lithium polymer battery (22.2V nominal). Analog sensors were read through a 10-bit analog to digital converter (ADC). The system is controlled by an on-board microcontroller such as AVR) and could be monitored by either USB and/or Bluetooth. All processing is performed on-board and power is supplied by a relatively small battery (mass=0.15 kg). The prototype is completely self-contained and does not require tethering.

Figure 7A:
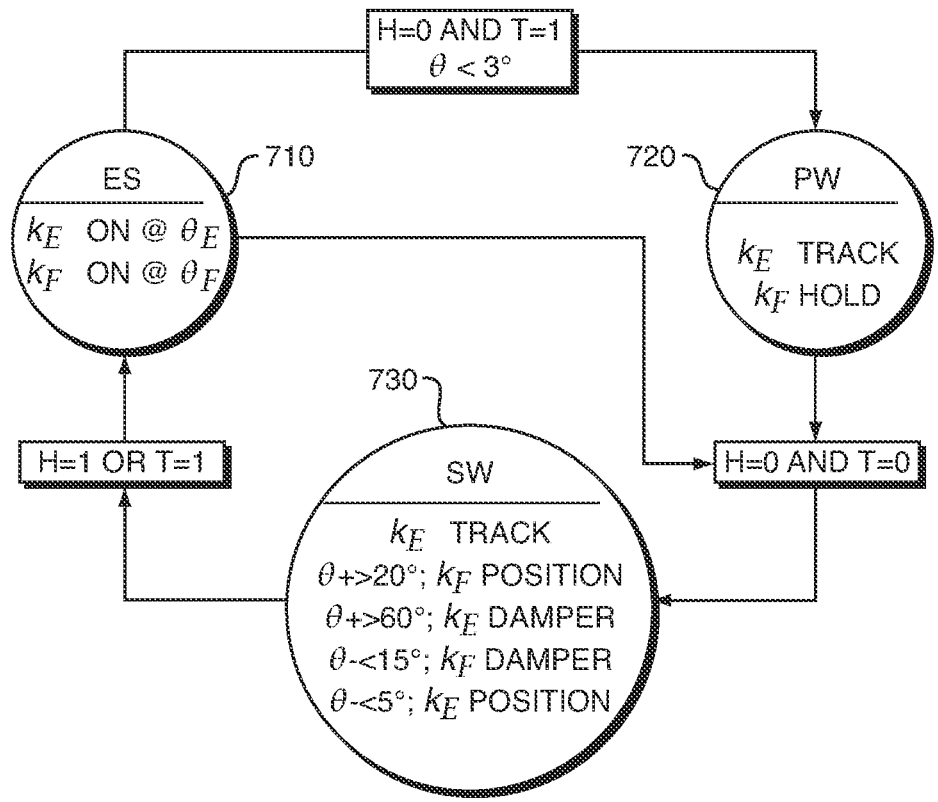
FIG. 7A is a schematic of a finite-state controller for level-ground walking implemented to replicate the intact knee behavior shown in FIGS. 1A-B, according to one aspect of the present invention.

Finite-State Control Strategy. A finite-state controller for level-ground walking was implemented to replicate the intact knee behavior shown in FIGS. 1A-B. This state machine is depicted in FIG. 7A. Three states are shown with control actions and transitional conditions. The three states of the controller are Early Stance (ES) 710, Pre-Swing (PW) 720 and Swing (SW) 730. A quasi-passive equilibrium point control was implemented for states ES 710 and PW 720, while during the SW state 730 variable-damping control was employed. Transitions between states were determined primarily by three measurements: heel ground contact, toe ground contact, and knee angle.

For state transition and identification, the system relied on the following variables:

Heel contact (H). H=1 indicates that the heel is in contact with the ground, and H=0 indicates the off-ground status.

Toe contact (T). T=1 indicates that the toe is in contact with the ground, and T=0 indicates the off-ground status.

Knee angle ($\theta$) is the relative angle of the knee joint. All knee angles are flexion angles. Angles $\theta_E$ and $\theta_F$ define the angles at which the extension and flexion springs become engaged during stance, respectively. Further, $\theta_+$ is the angle of the knee during swing flexion, and $\theta_-$ is the angle of the knee during swing extension.

Descriptions for each state are as follows: Early Stance (ES) 710 begins at Heel Strike (HS). When the heel contacts the ground (H=1), the extension motor shaft is locked using a high PD gain control with a desired shaft velocity equal to zero. The extension spring is then engaged with a spring equilibrium angle equal to the knee's position at heel strike $\theta_E$. The extension spring then stores energy during early stance knee flexion in preparation for knee extension. During knee flexion, the equilibrium point of the flexion spring $\theta_F$ is servoed via position control to closely track the linear carriage linked to the knee output joint. When the knee is maximally flexed in early stance, the knee begins to extend, and the flexion motor shaft is locked. The flexion spring then becomes engaged with a spring equilibrium angle equal to the knee's position at maximum knee flexion $\theta_F$. Initially, energy is released from the extension spring and subsequently stored in the flexion spring.

Pre-Swing (PW) 720 begins as the heel leaves the ground (H=0) and the knee angle becomes small ($\theta<3°$). In this state, the equilibrium point of the extension spring $\theta_E$ is position controlled under zero load, tracking closely the linear carriage as the knee flexes in preparation for the swing phase. The flexion spring keeps holding its current equilibrium position $\theta_F$ (motor shaft locked). Thus, as the knee flexes through-out PW, the energy stored in the flexion spring is released.

Swing (SW) 730 begins at toe off (T=0). The extension spring equilibrium angle $\theta_E$ continues to track the knee angle under zero load. As the knee flexes beyond 20 degrees ($\theta_+>20°$) the flexion spring equilibrium angle $\theta_F$ is servoed under zero load to a position corresponding to $\theta=15°$. When the knee flexes past 60 degrees ($\theta_+>60°$), the extension spring is engaged. A low gain damping control on the extension motor shaft causes the extension motor and transmission to backdrive, acting as a variable damper to reduce hyper-flexion of the knee. Once the knee begins to extend and has an angle of less than 60 degrees ($\theta_-<60°$), the extension spring equilibrium angle $\theta_E$ then once again tracks the linear carriage under zero load to follow the knee throughout its extension. As the knee continues to extend past 15 degrees in late swing, the flexion spring is engaged. Here again, a low gain damping control on the flexion motor shaft causes the flexion motor and transmission to backdrive, acting as a variable damper to smoothly decelerate the swing leg until the flexion spring reaches an equilibrium angle $\theta_F$ is of 3 degrees. When the knee extends in swing beyond 5 degrees ($\theta\_<5°$) the extension spring equilibrium angle $\theta_E$ is servoed to 3 degrees, in preparation for engagement and energy storage at heel strike of the subsequent gait cycle.

Figure 7B:
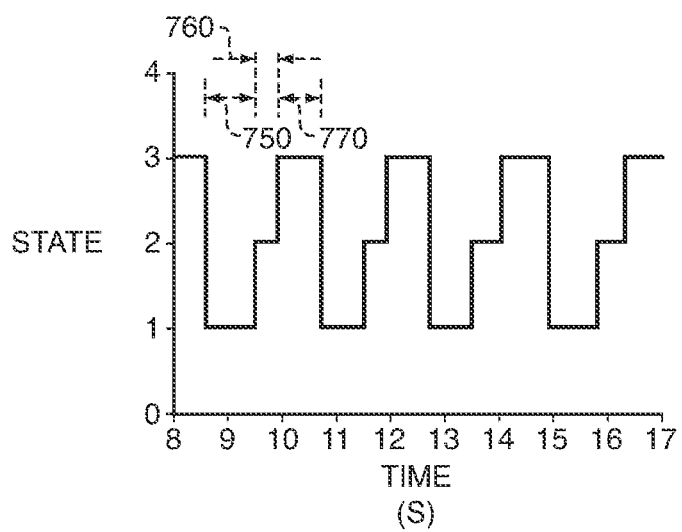
FIG. 7B graphically depicts knee finite-state control transitions during amputee level-ground walking for the controller of FIG. 7A.

The finite-state control diagram indicating transitions for the state machine of FIG. 7A is shown in FIG. 7B. The diagram in FIG. 7B exemplifies controller state transition performance for three consecutive, level-ground walking cycles of the implemented controls strategy in the embodiment of FIGS. 4A-C, 5, and 6. The control states for level-ground walking are defined as follows: Early Stance (ES-State 1) 750, Pre-Swing (PW-State 2) 760, and Swing (SW-State 3) 770. The system went through the state sequence 1-2-3 (ES-PW-SW) for each walking cycle. The controller transitions robustly from states 1-2-3 across three consecutive walking cycles.

Figure 8A:
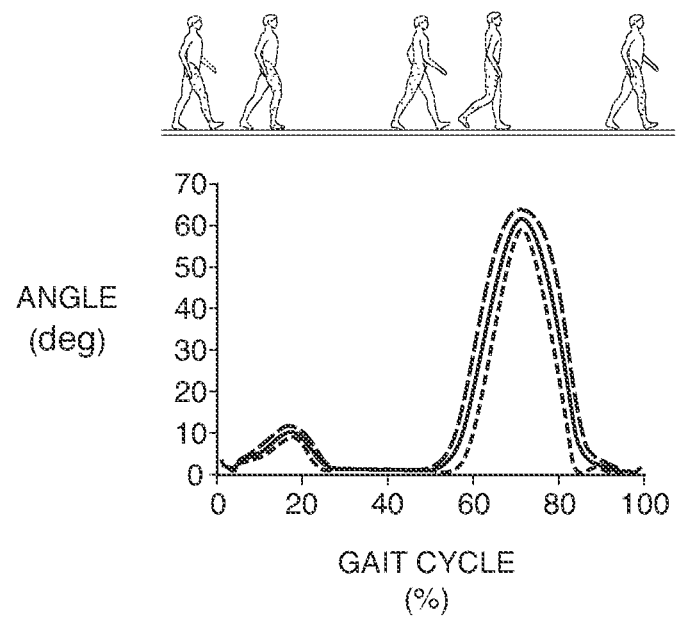
FIGS. 8A-E depict results obtained from a preliminary gait evaluation of the powered prosthesis during level-ground walking at a self-selected speed, according to one aspect of the present invention.
Figure 8B:
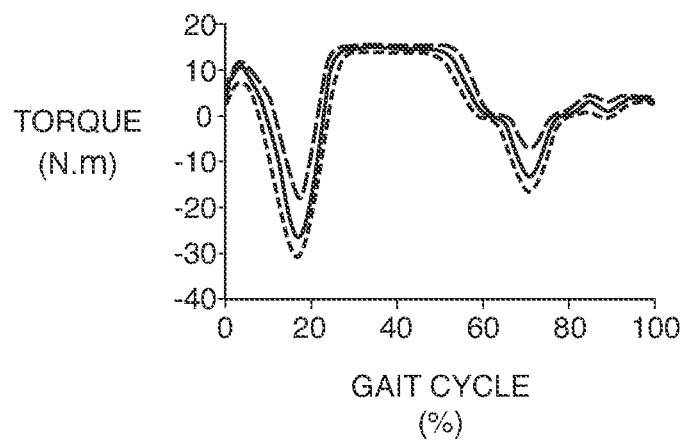
Figure 8C:
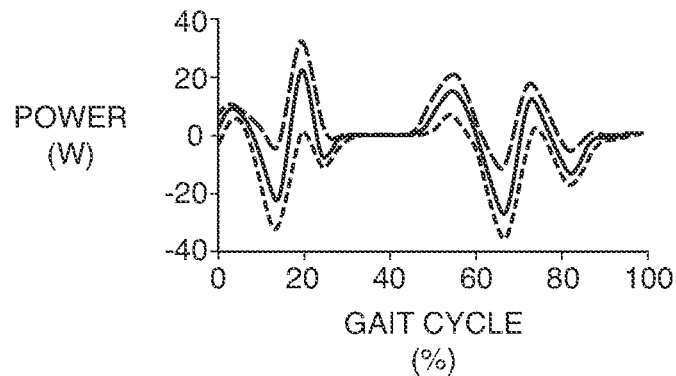
Figure 8D:
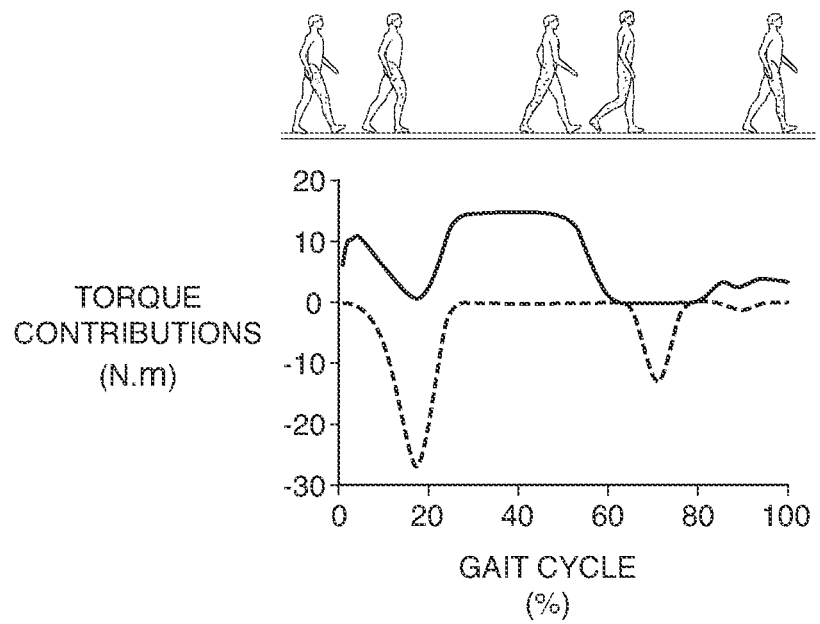
Figure 8E:
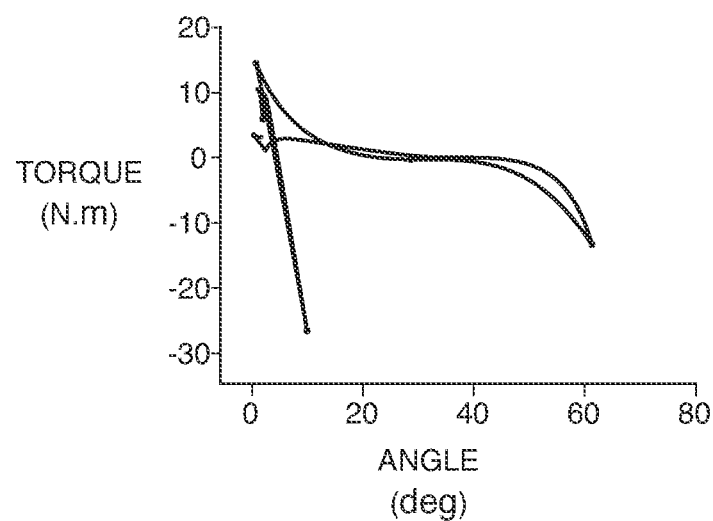

Results obtained from a preliminary gait evaluation of the powered prosthesis during level-ground walking at a self-selected speed (0.81 msec) are presented in FIGS. 8A-E. Prosthetic knee angle (FIG. 8A), net torque (FIG. 8B), and power (FIG. 8C) are plotted versus percent gait cycle (mean is solid line; one standard deviation is dashed line; N=10 gait trials) for level-ground walking (amputee participant mass=97 kg; walking speed=0.81 m/sec). In FIG. 8D, the torque contributions from the extension (lower line) and flexion (upper line) springs of the series-elastic actuators are plotted. In FIG. 8E, knee torque is plotted versus knee angular position, showing two characteristic stiffnesses during stance.

These prosthetic knee values show qualitative agreement with intact knee mechanics shown in FIG. 1A from a weight and height-matched non-amputee. Similar to the knee kinematics of an intact knee, as shown in FIG. 8A, the prosthetic knee exhibits early stance knee flexion (peak flexion angle of ~14.5 degrees) following by knee extension. At terminal stance, the prosthetic knee undergoes rapid knee flexion in preparation for the swing phase. During the swing phase, the knee extends to a peak flexion angle of ~61 degrees, before extending forward prior to heel strike. As shown in FIGS. 8B and 8C, prosthetic knee torque and power are negative during early stance knee flexion. For the intact knee data shown in FIG. 1A, knee torque and power are initially positive following heel strike, but quickly become negative as the knee continues to flex. The prosthetic knee exhibited a similar behavior at the beginning of early stance as shown in FIG. 8B. This occurred because the amputee initially extended the knee right at heel strike, engaging the flexion spring and but quickly continued to knee flex engaging the extension spring. Compressing the extension spring immediately after heel strike helped limit the knee from undergoing excessive buckling so as to better ensure the amputee wearer's safety. For both the intact and prosthetic knee, during stance knee extension, torque is initially negative and then becomes positive, and knee power is initially positive and then becomes negative. Still further, during pre-swing, torque and power are initially positive and then become negative in preparation for the swing phase. During swing, for both intact and prosthetic knees, power is generally negative to limit peak knee flexion (negative torque) and then to smoothly decelerate the swinging leg during swing extension (positive torque).

The torque contributions from each unidirectional, series-elastic actuator are plotted in FIG. 8D versus percent gait cycle. The flexion spring is briefly engaged right after heel strike due to amputee's short knee extension. At the instant stance knee flexion occurs, the extension spring is engaged, similar to the prosthetic knee model. During stance flexion, the flexion spring loses its energy quickly as it closely tracks the linear carriage linked to the knee output joint. Subsequently, the flexion spring is engaged again at peak knee flexion during early stance and stores energy during stance extension and pre-swing. In swing, the extension motor at peak knee flexion, and the flexion motor at terminal stance, are actively back driven to limit peak knee flexion and to smoothly decelerate the swinging leg at terminal stance, respectively. In FIG. 8E, prosthetic knee torque is plotted versus knee angular position. Like the intact human knee (FIG. 1B), the prosthesis has two characteristic stiffnesses during stance. During early stance flexion and extension phases, knee stiffness is relatively greater than during pre-swing.

The prosthesis knee embodiment of FIGS. 4A-C, 5, and 6 takes advantage of the incorporated series-elastic components in combination with the variable-impedance control to minimize the electrical energy during walking. With this strategy the knee behavior demonstrates agreement between prosthesis and intact knee mechanics. With the combination of mechanical design architecture and control, the prosthesis' electrical motors do not perform positive work on the knee joint during level-ground walking, resulting in modest electrical power requirements.

Because of the variable-impedance prosthetic control during level-ground walking, the knee prosthesis' electrical power requirements low (8 Watts electrical) during steady-state walking trials at an average walking speed of 0.81 msec. Using step count monitoring systems, researchers have determined that active unilateral leg amputees walk 3060±1890 steps per day. To estimate motor electrical power requirements (power=current*voltage), onboard motor current sensing was used to directly measure the current of each motor, and to estimate motor voltages, motor speeds, motor speed constants, and motor resistances were used. Assuming the case of an amputee walking for 5000 steps at a moderate walking speed, the size of the onboard battery can be estimated. A 0.13 kg Li-Polymer battery for example (energy density 165 Watt-hrs/kg), would enable 5000 steps of powered walking (8 Watts*1.95 sec/cycle*5000 cycles=78 kJoules). This battery mass is over 5-fold smaller than the required battery other commercially powered knees.

Figure 9A:
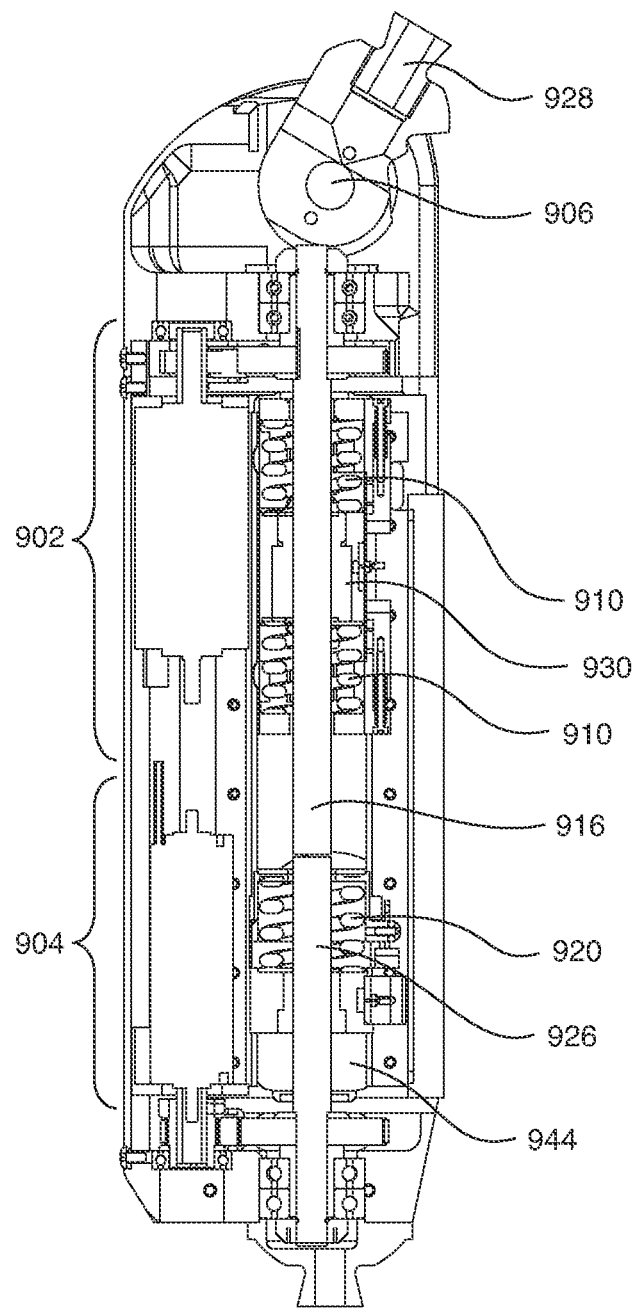
FIGS. 9A-C are lateral view, sagittal plane cut view, and posterior view schematics, respectively, of the mechanical design of another exemplary embodiment of an active knee prosthesis, according to the present invention.
Figure 9B:
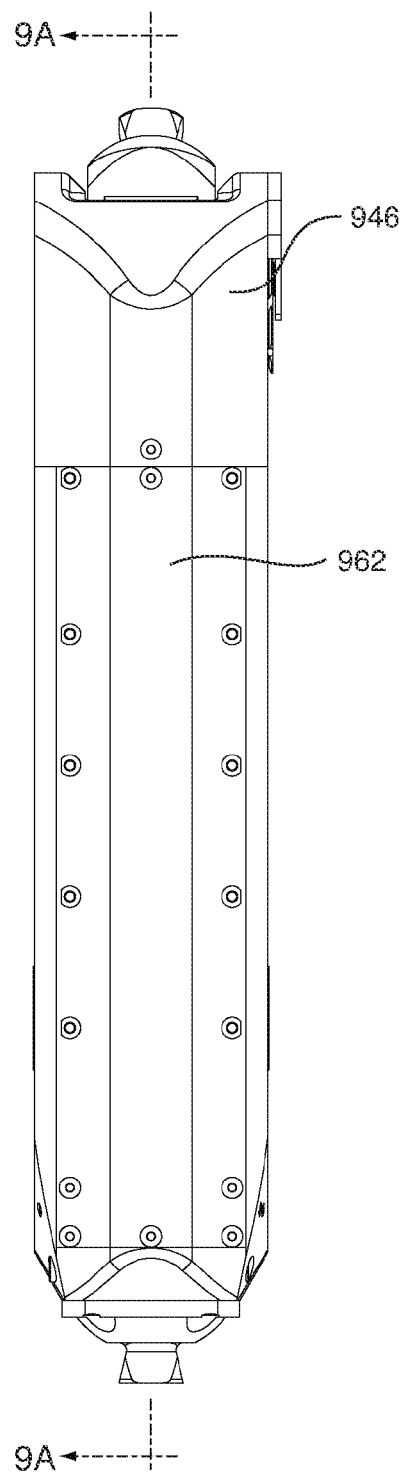
Figure 9C:
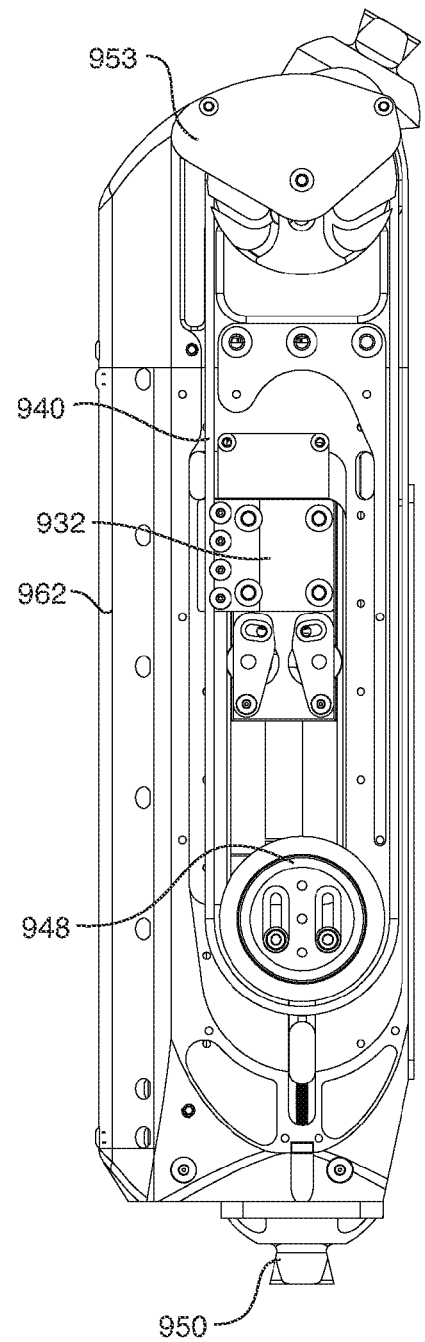
Figure 10:
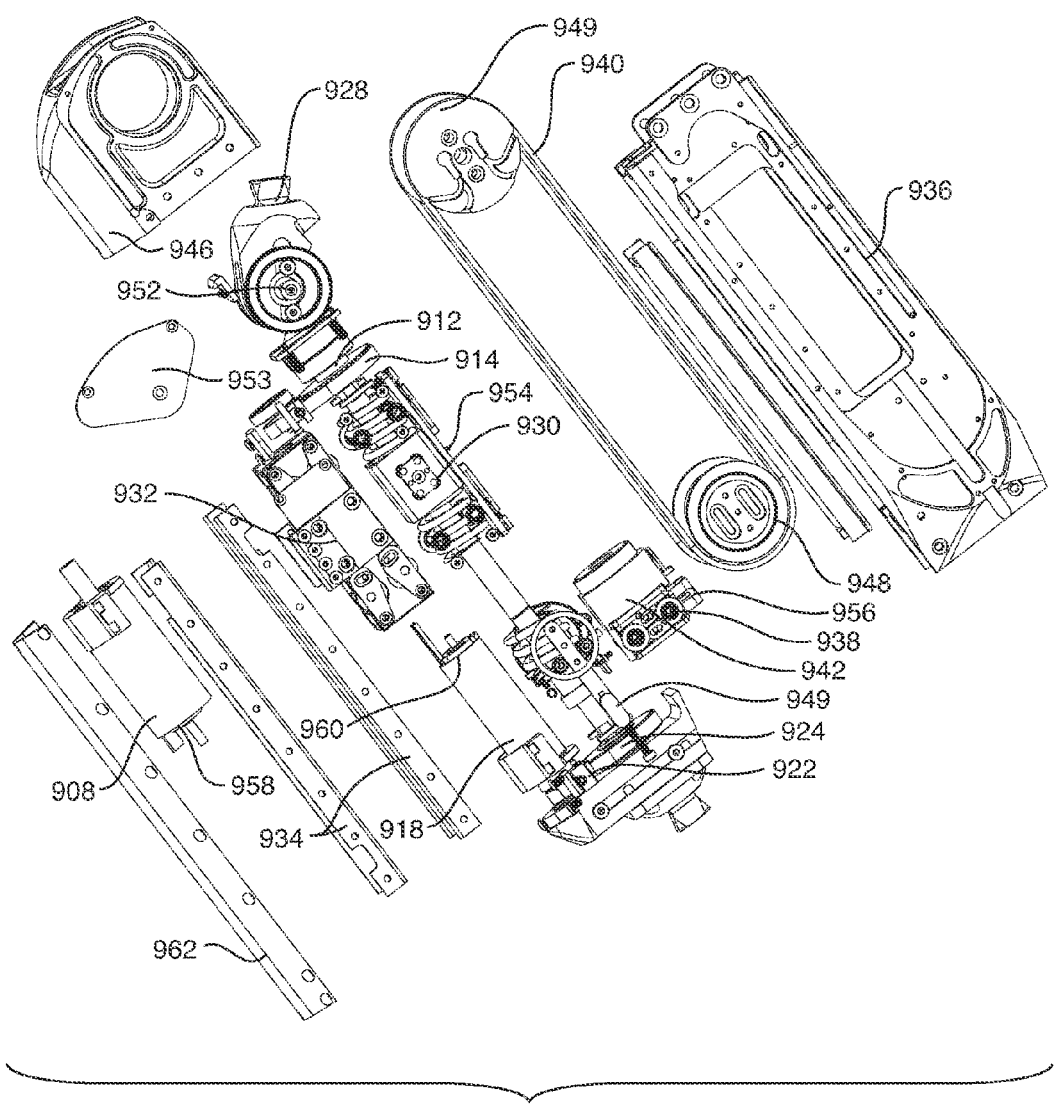
FIG. 10 is an exploded view of the main components of an exemplary embodiment of the active knee prosthesis of FIGS. 9A-C.

In a second preferred embodiment, shown in FIGS. 9A-C, an active knee prosthesis comprises two actuators arranged in an agonist antagonist architecture. FIG. 10 is an exploded view of the main components of the exemplary embodiment of an active knee prosthesis of FIGS. 9A-C. In this embodiment of an active knee prosthesis according to the invention, the two actuators are one extension series elastic actuator 902 and one flexion actuator 904. Extension actuator 902 is bidirectional and flexion actuator 904 is unidirectional. Extension actuator 902, proximal to knee joint 906 of prosthesis, consists of extension motor 908 and a set of pre-compressed series springs 910, connected via a transmission. The extension transmission consists of timing pulley set 912 and belt 914 drive system coupled to precision ball-screw 916 drive. Unidirectional flexion actuator 904 of the knee prosthesis consists of flexion motor 918 and series spring 920, connected via a transmission. The flexion transmission consists of timing pulley set 922 and belt 924 drive system coupled to lead-screw 926 drive. Extension actuator 902 and flexion actuator 904 can be used independently to control the knee joint 906 angle at which series springs 910, 920 can be engaged.

The extension actuator's 902 electric motor 908 can be a brushed DC motor (such as Maxon's RE40 motor) or brushless DC motor (such as Maxon's EC-powermax 30). The extension motor directly drives a timing pulley-belt drive 914, 928 mechanism. This mechanism has a 1:2 transmission ratio. Timing pulley-belt drive mechanism 914, 928 actuates the rotation of ball-screw 916 (such as Nook industries, 10×3 mm). When ball-screw 916 of extension actuator 902 is rotated, there is a linear displacement of coupled ball-nut housing 930. Ball nut housing 930 is directly attached to extension series-elastic spring cage 932. Extension series-elastic spring cage 932 securely contains spring set 910 of two identical pre-compressed passive mechanical springs whose stiffness match that of the model's extension actuator. Thus, when there is a linear displacement of coupled ball-nut housing 930, extension series elastic cage 932 has a linear displacement. Ball-nut housing 930 moves along two linear steel guide rails 934. Each of the rails is attached to a corresponding lateral wall housing 936. Spring cage 932 moves along the guide rails supported by its incorporated roller bearings 938. Extension actuator 902 is directly coupled to the rotary motion of knee joint 906, as it is attached to steel cable drive system 940.

The flexion actuator's 904 electric motor 918 can be a brushed DC motor (such as Maxon's RE40, RE30 motors) or brushless DC motor (such as Maxon's EC-powermax 30 or 22). The extension motor directly drives timing pulley-belt drive 922, 924 mechanism. This mechanism has a 1:2 transmission ratio. Pulley-belt drive mechanism 922, 924 actuates the rotation of lead-screw 926 (such as Nook industries, 10×3 mm). When lead-screw 926 of flexion actuator 904 is rotated, there is a linear displacement of coupled ball-nut housing 942. Ball-nut housing 942 is directly attached to flexion series spring cage 944. Flexion series spring cage 944 securely contains flexion spring 920. Thus, when there is a linear displacement of coupled ball-nut housing 942, the flexion series spring cage can have a linear displacement. Ball-nut housing 942 moves along two linear steel guide rails 934 with minimal friction due to rollers 938 incorporated in the ball-nut housing. Flexion actuator 904 is not directly coupled to the rotary motion of knee joint 906, however it can flex the knee when in action, back-drives the extension's series elastic spring cage 932.

Knee joint 932 is coupled to a set of two steel cable drives 940 connected to the extension's series elastic spring cage 932. The series elastic-cage is supported and guided by two steel precision guide rails 934. Steel cables 940 allow the coupling of linear displacement from series elastic spring cage 932 to the rotary motion of knee joint 906.

The two ends of each of steel cables 940 are attached to the knee joint's driving hubs 944. Driving hubs 944 are supported by knee joint housing 946. Each cable loops around its corresponding joint pulley 948 located on each side of the knee, distally from knee joint 906. Each lateral joint pulley 948 has its axis attached to its corresponding lateral wall 936. Each cable drive 940 can be independently tensioned by adjusting lateral joint pulley 948 by tuning the corresponding cable tensioner 949. Each of the series-elastic actuators 902, 904 is capable of providing sufficient power for both level-ground walking and more energetically expensive tasks such as stair ascent.

All actuation mechanisms are fully supported by an aluminum structure that corresponds to the assembly of lateral knee walls 936, upper pyramid adaptor 928 and lower pyramid adaptor 950. This structure provides a support frame that resembles the lower limb anatomical envelope. Lower pyramid adaptor 950 allows conventional and advanced robotic foot-ankle prosthesis to be attached to the knee prosthesis. The standard prosthetic upper pyramid adaptor 928 allows the knee prosthesis to be attached to a regular transfemoral socket and be worn by an above-knee amputee. The design of the prosthesis facilitates its maintenance as it as detachable side and front covers that allow easy access to the driving actuators and mechanisms.

The design parameters for knee size, angular range, and maximum torque values for the embodiment of FIGS. 9A-C and 10 are listed in Table 3.

TABLE 3

| | |
|---|---|
| Height | 32.8 cm |
| Medio-lateral width | 6.8 cm |
| Anterior-posterior width | 7 cm |
| Total weight | 2.7 Kg |
| Flexion angle range | 0-125 deg |
| Output torque | 130 Nm |

The knee's intrinsic sensory system provides feedback to the onboard control electronics. These sensors are listed in Table 4.

TABLE 4

| Measurement | Sensor |
|---|---|
| Knee angle | Digital encoder |
| Motor displacement | Digital encoder |
| Heel strike | Strain gauge |
| Spring compression | Hall effect |
| Heel/Toe contact | Force sensitive resistor foot pad |
| Orientation/acceleration | Inertial measurement unit |

The sensors monitor the angular displacement of knee joint 906, the displacement and deformation of each series elastic element and the force/contact interaction of the knee with the environment (ground) during walking.

The angular displacement of the knee is measured directly with absolute encoder 952 located at knee joint 906. This sensor 952 is mounted on encoder housing 953 that aligns with the joint rotation. The compression of each the series elastic actuator's springs 910, 920 is measured with corresponding hall-effect sensor 954, 956. These sensors measure the magnetic field change that occurs when there is a change to the proximity of a magnet attached to each of spring cages 932, 944 while springs 910, 920 are being compressed. The rotation of each motor is measured by motor digital encoder 958, 960 attached to the back of corresponding motor 908, 918. The interaction with the ground is measured with a force sensitive footpad (not pictured). This footpad allows detection of when the leg is in contact with the walking surface, and it allows the controller to determine what gait phase the user wearing the robotic knee prosthesis is in. Another method used to measure interaction with the ground is with the use of strain gauges mounted on the frame of the knee (specifically in shin cover 962) and through instrumented lower pyramid 950. This sensory information will provide information on forces and torques that interact in the knee and can provide information to calculate torque at the knee joint. This information will assist the controller in determining the gait phase. Another sensor that is considered for this embodiment is the use of an inertial measurement unit (not pictured) which attaches to the knee's main frame, allowing the controller identify orientation and acceleration during the gait cycle.

The electronic suite is self-contained, providing autonomy to the knee prosthesis (non-tethered control). The electronics have been implemented in a group of five printed circuit boards (PCB's) that are assembled on the lateral and back walls of the knee. Two of these boards are dedicated to the control of the actuators, one board is in charge of overseeing the overall knee control strategy, one board is dedicated to the connection and communication with a an external monitoring PC/laptop system and a final board that will be in charge of processing data of an inertial measurement unit installed in the knee. The electronic suite is based on PIC microcontroller technology and is powered by a six cell lithium polymer battery with a 22.2 V nominal supply. Motor boards include brushless controllers with controls up to 20 KHz. The system behavior can be monitored and updated via USB or wirelessly via wi-fi interconnection.

Finite-state control strategy. Using five phases during the gait cycle, a knee control strategy for level ground walking has been established that exploits the quasi-passive knee model in order to mimic knee biomechanics with minimal energy consumption:

Beginning at heel strike, the stance knee begins to flex slightly (~15 degrees). This Stance Flexion phase allows for shock absorption upon impact. During this phase, the knee's extension actuator will engage its series elastic components by maintaining the spring equilibrium position as energy is stored during knee flexion. The motor in this case is acting as the engaging clutch.

After reaching maximum stance flexion, the knee joint begins to extend (~15% gait cycle), until maximum stance extension (MSE) is reached (~42% gait cycle). This knee extension period is called the Stance Extension phase. During Stance Extension, the flexion actuator positions its series spring such that when the knee starts to extend, energy is stored, allowing the energy in the extension spring to be transferred. This energy transfer allows modulation of the stiffness during stance. Is important to mention that as the flexion actuator's transmission includes a lead screw, as soon as it positions its linear spring, the motor doesn't provide anymore positive power, thus, minimizing overall energy consumption. This is effectively using the model's clutch engagement behavior in a "normally closed" setting.

During late stance or Pre-Swing (from ~42% to ~62% gait cycle), the knee of the supporting leg begins its rapid flexion period in preparation for the Swing phase. During Pre-Swing, as the knee begins to flex in preparation for toe-off, the energy stored in the flexion spring gets released assisting the user before toe-off.

As the leg leaves the ground, the knee continues to flex. At toe-off, the Swing Flexion phase of gait begins. Throughout this period (from 62% to 73% gait cycle), knee power is generally negative as the knee's torque impedes knee rotational velocity. Thus, during Swing Flexion, the knee's extension actuator is utilized as a regenerative element, the energy that is dampened during the swing phase can be stored in the on-board battery as the actuator is back driven and the leg is repositioned to start a new gait cycle.

After reaching a maximum flexion angle (~60 degrees) during Swing, the knee begins to extend forward. During Swing Extension (from ~73% to ~100% gait cycle), knee power is generally negative to decelerate the swinging leg in preparation for the next stance period. In this phase the extension actuator is utilized as an element to provide energy regeneration and improve the energetic efficiency of the knee prosthesis. During this phase, the flexion motor repositions the linear spring in preparation for the new gait cycle.

Prosthetic Knee Design for Variable-Speed Walking The active prosthetic knee embodiments described are intended for amputees with a capacity to ambulate at a K3 level (i.e. having the ability or potential for ambulation with variable cadence). In order to have a prosthetic knee that can adapt to amputee speed variations and still maintain an optimal level of energetic economy, both series-elastic components have to be non-linear and adjusted to the amputee's weight.

Figure 11A:
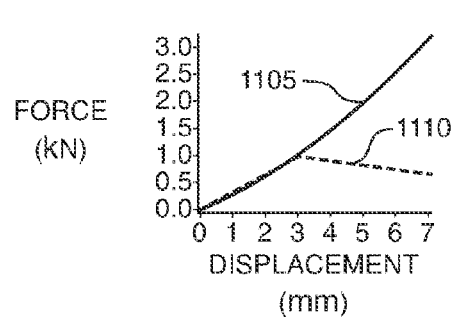
FIG. 11A is a plot of the results of an optimized non-linear polynomial fit for the force vs. displacement behavior of the series-elastic elements of an active knee according to the present invention.

To evaluate speed adaptation, the variable-impedance knee model was fitted to biomechanical data from an intact subject walking at 1.0 m/s, 1.3 m/s and 1.6 m/s speeds using the optimization scheme previously described. The optimization results provided linear stiffness values (at each walking speed) for both series-elastic components, including their engagement angles during the walking cycle. For each spring and walking speed, the maximum force-displacement data pairs were selected first. By plotting all data pairs in the same force vs. displacement space, it was then possible to estimate the optimal non-linear spring functions for the flexion and extension springs. FIG. 11A is a plot of the results of an optimized non-linear polynomial fit for the force vs. displacement behavior of the series-elastic elements of an active knee according to the present invention. In particular, a second order polynomial fit was implemented for the model's extension spring 1105, and a piece wise polynomial fit for the flexion spring 1110.

Figure 11B:
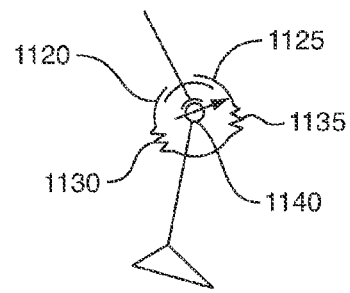
FIG. 11B depicts an exemplary embodiment of a variable-impedance prosthetic knee model for variable-speed walking, according to one aspect of the invention.

As suggested by the data in FIG. 11A, for a variable-speed walking application the extension series-elastic component of FIG. 2 has to be replaced by a non-linear hardening elastic component and the flexion component of FIG. 2 has to be replaced by a softening spring. FIG. 11B depicts an exemplary embodiment of a variable-impedance prosthetic knee model for variable-speed walking, according to one aspect of the invention. As shown in FIG. 11B, the model comprises two mono-articular series-elastic clutches 1120, 1125, two non-linear springs 1130, 1135, and variable-damping element 1140.

Figure 11C:
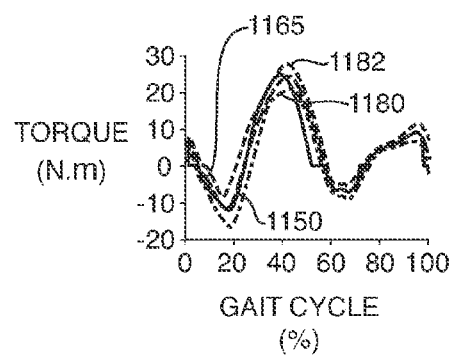
FIGS. 11C-E graphically depict prosthetic knee model output torque compared to the biological knee torque data for three different walking speeds, using the model of FIG. 11B.
Figure 11D:
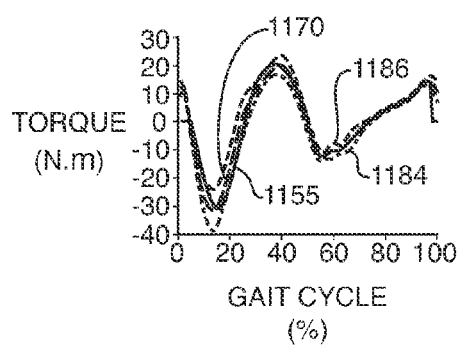
Figure 11E:
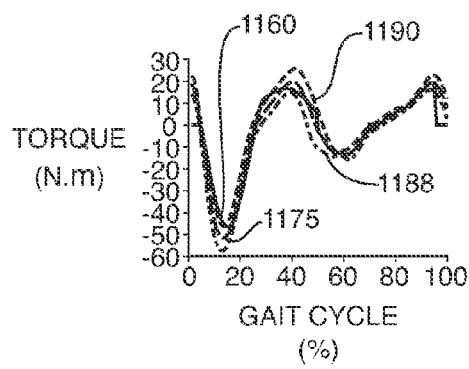

Utilizing these non-linear spring functions, the prosthetic knee model output torque was compared to the biological knee torque data. FIGS. 11C-E show this comparison for the three different walking speeds using the model shown in FIG. 11B. In FIGS. 11C-E, the net torque output of the optimized knee model 1150, 1155, 1160 is compared to the torque profile of an intact human knee joint, with both mean 1165, 1170, 1175 and one standard deviation 1180, 1182, 1184, 1186, 1188, 1190 shown for each speed (N=10 gait trials). Goodness of fit for the model is provided by the coefficient of determination $R^2$ at each walking speed. Biological data are from a study participant (mass=66.2 kg) with intact limbs walking at three different speeds: 1.0 m/s (FIG. 11C); 1.3 m/s (FIG. 11D); and 1.6 m/s (FIG. 11E). Walking speeds within a ±5% interval for each selected speed were accepted.

It will be clear to one of skill in the art of the invention that the prosthetic knee model for variable-speed walking may be physically implemented in a manner similar to the implementation of the embodiments described for the model of FIG. 2, using components and materials that will be readily apparent to one of skill in the art, and that any of the variations and modifications that would be suitable for the embodiments of FIGS. 4A-C and 9A-C would also be suitable for use in an implementation of the model of FIG. 11B.

Further, while preferred embodiments of the invention are disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

What is claimed is:

1. A powered artificial knee comprising, in combination:

a knee joint, the knee joint being rotatable and coupleable to a first artificial upper leg member and a second artificial lower leg member;

an agonist-antagonist actuator, comprising
- a series-elastic flexion actuator, connected to the knee joint in parallel with the first leg member, for applying a force to cause rotation of the knee joint, resulting in flexion of the first leg member, the flexion actuator comprising a series combination of a flexion motor and a flexion elastic element, and further comprising a flexion motor shaft;
- a series-elastic extension actuator, connected to the knee joint in parallel with the first leg member, in opposition to the flexion actuator, for applying a force to cause rotation of the knee joint, resulting in extension of the first leg member, the extension actuator comprising a series combination of an extension motor and an extension elastic element, and further comprising an extension motor shaft; and
- a controller configured for independently energizing the flexion motor and the extension motor at different times to control position, impedance, and nonconservative torque of the knee joint; and at least one sensor configured to provide feedback to the controller;

wherein:
- the controller is responsive to sensor feedback indicating three states of a levelground walking gait cycle, Early Stance, Pre-Swing, and Swing, and is configured to employ quasi-passive equilibrium point control during the Early Stance state and the PreSwing state and variable-damping control during the Swing state;
- the knee joint defines a knee joint angle between the first and second leg members, which knee joint angle may vary;
- the extension elastic element has an extension equilibrium angle that may vary;
- the flexion elastic element has a flexion equilibrium angle that may vary; and the controller is configured such that:

during Early Stance,
- the extension motor shaft is locked,
- the extension elastic element is engaged with the extension equilibrium angle equal to the knee joint angle at Heel Strike,
- during Early Stance knee flexion, the extension elastic element stores energy,
- the flexion equilibrium angle is position-controlled, and
- the flexion motor shaft is locked when the knee joint is maximally flexed and begins to extend,
- after which the flexion elastic element is engaged with the flexion equilibrium angle equal to the knee joint angle at maximum knee flexion, so that energy is then released from the extension elastic element to be stored in the flexion elastic element;

during Pre-Swing,
- the extension elastic element equilibrium angle is position-controlled under zero load,
- the flexion elastic element maintains the flexion equilibrium angle equal to the knee joint angle at maximum knee flexion, and
- the flexion motor shaft remains locked, and the energy stored in the flexion elastic element is released; and during Swing,
- the extension equilibrium angle remains position-controlled under zero load,
- the flexion equilibrium angle is set under zero load to a knee joint angle minimum threshold,
- the extension elastic element is engaged when the knee joint flexes past a knee joint angle maximum threshold,
- a low gain damping control on the extension motor shaft causes the extension motor to act as a variable damper to reduce hyper-flexion of the knee joint,
- when the knee extends and has an angle of less than the knee joint angle maximum threshold, the extension equilibrium angle tracks the knee joint angle under zero load,
- as the knee extends past a knee joint angle minimum threshold, the flexion elastic element is engaged,
- a low gain damping control on the flexion motor shaft causes the flexion motor to act as a variable damper to decelerate the second artificial lower leg member until the flexion equilibrium angle is
- at a flexion equilibrium angle minimum threshold, and
- the extension equilibrium angle is set to an extension equilibrium angle minimum threshold in preparation for a subsequent gait cycle.

* * * * *